(12) United States Patent
Akbari

(10) Patent No.: US 9,926,607 B2
(45) Date of Patent: Mar. 27, 2018

(54) BREAST CANCER BIOMARKERS AND METHODS OF USING SAME

(71) Applicant: Women's College Hospital, Toronto (CA)

(72) Inventor: Mohammad R. Akbari, Toronto (CA)

(73) Assignee: Women's College Hospital, Toronto (CA)

( * ) Notice: Subject to any disclaimer, the term of this patent is extended or adjusted under 35 U.S.C. 154(b) by 0 days.

(21) Appl. No.: 15/078,925

(22) Filed: Mar. 23, 2016

(65) Prior Publication Data

US 2016/0281173 A1    Sep. 29, 2016

Related U.S. Application Data

(60) Provisional application No. 62/138,874, filed on Mar. 26, 2015.

(51) Int. Cl.
| | |
|---|---|
| *A61K 48/00* | (2006.01) |
| *C12Q 1/68* | (2018.01) |
| *A61K 31/4745* | (2006.01) |
| *C12N 15/113* | (2010.01) |
| *A61K 31/7088* | (2006.01) |

(52) U.S. Cl.
CPC ........ *C12Q 1/6886* (2013.01); *A61K 31/4745* (2013.01); *A61K 31/7088* (2013.01); *C12N 15/1135* (2013.01); *C12N 15/1137* (2013.01); *C12Y 306/01* (2013.01); *C12Y 306/04012* (2013.01); *C12N 2310/14* (2013.01); *C12Q 2600/118* (2013.01); *C12Q 2600/136* (2013.01); *C12Q 2600/156* (2013.01); *C12Q 2600/158* (2013.01); *C12Q 2600/178* (2013.01)

(58) Field of Classification Search
CPC ..................................................... A61K 48/00
See application file for complete search history.

(56) References Cited

U.S. PATENT DOCUMENTS

2014/0302042 A1* 10/2014 Chin .................... C12Q 1/6886
                                                                424/139.1

OTHER PUBLICATIONS

Couch, F.J. et al., Two decades after BRCA: setting paradigms in personalized cancer care and prevention, Science, Mar. 28, 2014, 343(6178):1466-70.
Miki, Y. et al., A strong candidate for the breast and ovarian cancer susceptibility gene BRCA1, Science, Oct. 7, 1994, 266(5182):66-71.
Wooster, R. et al., Identification of the breast cancer susceptibility gene BRCA2, Nature, Dec. 21-28, 1995, 378(6559):789-92.
Rahman, N., et al., Breast Cancer Susceptibility Collaboration (UK), Easton DF, Stratton MR. PALB2, which encodes a BRCA2-interacting protein, is a breast cancer susceptibility gene, Nat Genet., Feb. 2007, 39(2):165-7.
Bogdanova, N., et al., Nijmegen Breakage Syndrome mutations and risk of breast cancer, Int J Cancer, Feb. 15, 2008, 122(4):802-6.
Meijers-Heijboer, H., et al., CHEK2-Breast Cancer Consortium. Low-penetrance susceptibility to breast cancer due to CHEK2(*)1100delC in noncarriers of BRCA1 or BRCA2 mutations, Nat Genet., May 2000, 31(1):55-9.
Renwick, A., et al., Breast Cancer Susceptibility Collaboration (UK), Easton DF, Stratton MR, Rahman N. ATM mutations that cause ataxia-telangiectasia are breast cancer susceptibility alleles, Nat Genet., Aug. 2006, 38(8):873-5.
Li, J., et al., PTEN, a putative protein tyrosine phosphatase gene mutated in human brain, breast, and prostate cancer, Science, Mar. 28, 1997, 275(5308):1943-7.
Malkin, D., et al., Germ line p53 mutations in a familial syndrome of breast cancer, sarcomas, and other neoplasms, Science, Nov. 30, 1990, 250(4985):1233-8.
Górski, B., et al., Founder mutations in the BRCA1 gene in Polish families with breast-ovarian cancer, Am J Hum Genet., Jun. 2000, 66(6):1963-8.
Cybulski, C., et al., A deletion in CHEK2 of 5,395 bp predisposes to breast cancer in Poland, Breast Cancer Res Treat., Mar. 2007, 102(1):119-22.
Steffen, J., et al., Germline mutations 657del5 of the NBS1 gene contribute significantly to the incidence of breast cancer in Central Poland, Int J Cancer, Jul. 15, 2006, 119(2):472-5.
Tonin, P.N., et al., Founder BRCA1 and BRCA2 mutations in French Canadian breast and ovarian cancer families, Am J Hum Genet., Nov. 1998, 63(5):1341-51.
Foulkes, W.D., et al., Identification of a novel truncating PALB2 mutation and analysis of its contribution to early-onset breast cancer in French-Canadian women, Breast Cancer Res., 2007, 9(6):R83.
Cybulski, C., et al., Mutations predisposing to breast cancer in 12 candidate genes in breast cancer patients from Poland, Clin Genet, Oct. 20, 2014 [Epub ahead of print].
Exome Variant Server, NHLBI GO Exome Sequencing Project (ESP), Seattle, WA (URL: http://evs.gs.washington.edu/EVS/) [Jul. 2014].
Pike, A.C., et al., Structure of the human RECQ1 helicase reveals a putative strand-separation pin, Proc Natl Acad Sci USA, Jan. 27, 2009, 106(4):1039-44.
Puranam, K.L., et al., Cloning and characterization of RECQL, a potential human homologue of the *Escherichia coli* DNA helicase RecQ, J Biol Chem, Nov. 25, 1994, 269(47):29838-45.
Seki, M., et al., Molecular cloning of cDNA encoding human DNA helicase Q1 which has homology to *Escherichia coli* Rec Q helicase and localization of the gene at chromosome 12p12, Nucleic Acids Res, Nov. 11, 1994, 22(22):4566-73.
Sharma, S., et al., Mechanisms of RecQ helicases in pathways of DNA metabolism and maintenance of genomic stability, Biochem J., Sep. 15, 2006, 398(3):319-37.

(Continued)

*Primary Examiner* — Kimberly Chong

(74) *Attorney, Agent, or Firm* — McCarthy Tétrault LLP

(57) ABSTRACT

The present invention provides breast cancer markers based on RECQL mutations, and related methods, uses, agents, and kits. The invention includes methods for determining the susceptibility of a subject to developing breast cancer, and methods for detecting, diagnosing, treating, and predicting responses to treatment for breast cancer.

15 Claims, 7 Drawing Sheets

(56) References Cited

OTHER PUBLICATIONS

Ellis, N.A., et al., The Bloom's syndrome gene product is homologous to RecQ helicases, Cell, Nov. 17, 1995, 83(4):655-66.
Yu, C.E., et al., Positional cloning of the Werner's syndrome gene, Science, Apr. 12, 1996, 272(5259):258-62.
Kitao, S., et al., Mutations in RECQL4 cause a subset of cases of Rothmund-Thomson syndrome, Nat Genet., May 1999, 22(1):82-4.
Sharma, S., et al., RECQL, a member of the RecQ family of DNA helicases, suppresses chromosomal instability, Mol Cell Biol., Mar. 2007, 27(5):1784-94.
Sharma, S., et al., Human RECQ1 is a DNA damage responsive protein required for genotoxic stress resistance and suppression of sister chromatid exchanges, PLoS One, Dec. 12, 2007, 2(12):e1297.
Futami, K., et al., Induction of mitotic cell death in cancer cells by small interference RNA suppressing the expression of RecQL1 helicase, Cancer Sci., Jan. 2008, 99(1):71-80.
Berti, M., et al., Human RECQ1 promotes restart of replication forks reversed by DNA topoisomerase I inhibition, Nat Struct Mol Biol., Mar. 2013, 20(3):347-54.
Parvathaneni, S., et al., Human RECQ1 interacts with Ku70/80 and modulates DNA end-joining of double-strand breaks, PLoS One, May 1, 2013, 8(5):e62481.
Popuri, V., et al., Human RECQL1 participates in telomere maintenance, Nucleic Acids Res., 2014, 42(9):5671-88.
Grepmeier, U., et al., Deletions at chromosome 2q and 12p are early and frequent molecular alterations in bronchial epithelium and NSCLC of long-term smokers, Int J Oncol., Aug. 2005, 27(2):481-8.
Koster, D.A., et al., Antitumour drugs impede DNA uncoiling by topoisomerase I, Nature, Jul. 2, 2007, 448(7150):213-7.
Montpetit, A., et al., Mutational and expression analysis of the chromosome 12p candidate tumor suppressor genes in pre-B acute lymphoblastic leukemia, Leukemia, Sep. 2004, 18(9):1499-504.
Arai, A., et al., RECQL1 and WRN proteins are potential therapeutic targets in head and neck squamous cell carcinoma, Cancer Res., Jul. 1, 2011, 71(13):4598-607.
Futami, K., et al., RecQL1 DNA repair helicase: A potential tumor marker and therapeutic target against hepatocellular carcinoma, Int J Mol Med., Apr. 2010, 25(4):537-45.
Bamford, S., et al., The COSMIC (Catalogue of Somatic Mutations in Cancer) database and website, Br J Cancer, Jul. 19, 2004, 91(2):355-8.
Henson, J.D., et al., Alternative lengthening of telomeres in mammalian cells, Oncogene, Jan. 21, 2002, 21(4):598-610.
Cho, N. W., et al., interchromosomal homology searches drive directional ALT telomere movement and synapsis, Cell, Sep. 25, 2014, 159(1):108-21.
Lucic, B., et al., A prominent β-hairpin structure in the winged-helix domain of RECQ1 is required for DNA unwinding and oligomer formation, Nucleic Acids Res., Mar. 2011, 39(5):1703-17.
Ghadirian, P., et al., Screening for BRCA1 and BRCA2 mutations among French-Canadian breast cancer cases attending an outpatient clinic in Montreal, Clin Genet,. Jan. 2014, 85(1):31-5.
Giroux, S., et al., Assessment of the prevalence of the 985A>G MCAD mutation in the French-Canadian population using allele-specific PCR, Clin. Genet,. Jun. 2007, 71(6):569-75.
Li, H, et al., Fast and accurate short read alignment with Burrows-Wheeler transform, Bioinformatics, 2009, 25:1754-60.
Cavallone, L. et al., Comprehensive BRCA1 and BRCA2 mutation analyses and review of French Canadian families with at least three cases of breast cancer, Fam. Cancer, 2010, 9: 507-517.
Arcand, S.L., et al., Germline TP53 mutations in BRCA1 and BRCA2 mutation-negative French Canadian breast cancer families, Breast Cancer Res. Treat., 2008, 108(3):399-408.
Tischkowitz, M., et al., Contribution of the PALB2 c.2323C>T [p. Q775X] founder mutation in well-defined breast and/or ovarian cancer families and unselected ovarian cancer cases of French Canadian descent, BMC Med. Genet., 2013, 14: 5.
Picard, http://picard.sourceforge.net.
McKenna, A., et al., The Genome Analysis Toolkit: a MapReduce framework for analyzing next-generation DNA sequencing data, Genome Res., 2010, 20:1297-303.
Ng, S.B., et al., Exome sequencing identifies the cause of a mendelian disorder, Nat. Genet., 2010, 42(1):30-5.
Prokofyeva, D., et al., Nonsense mutation p.Q548X in BLM, the gene mutated in Bloom's syndrome, is associated with breast cancer in Slavic populations, Breast Cancer Res. Treat., Jan. 2013, 137(2):533-9.
Sokolenko, A.P., et al., High prevalence and breast cancer predisposing role of the BLM, c.1642 C>T (Q548X) mutation in Russia, Int. J. Cancer, Jun. 15, 2012, 130(12):2867-73.
Siitonen, H.A., et al., Molecular defect of RAPADILINO syndrome expands the phenotype spectrum of RECQL diseases, Hum. Mol. Genet., Nov. 1, 2003, 12(21):2837-44.
Van Maldergem, L., et al., Revisiting the craniosynostosis-radial ray hypoplasia association: Baller-Gerold syndrome caused by mutations in the RECQL4 gene, J. Med. Genet., Feb. 2006, 43(2):148-52.
Scott, K. et al, Pro-invasion metastasis drivers in early stage melanoma are oncogenes, Cancel Cell, Jul. 12, 2011; 20(1):92-103.

\* cited by examiner

FIG. 4

| Mutation (DNA)* | Exon | Protein Change | Frequency FC | | Frequency Polish | | Frequency NHLBI exome data‡ |
|---|---|---|---|---|---|---|---|
| | | | Cases | Controls | Cases | Controls | |
| *Discovery Phase, whole exome sequencing of high-risk BC cases* | | | | | | | |
| c.132_135delGAAA | 3 | p.Lys45fs | 1/51 | N/A | Nil | N/A | 0/4,300 |
| c.426delT | 5 | p.Ser142fs | 1/51 | N/A | Nil | N/A | 0/4,300 |
| c.1138A>T | 10 | p.Lys380* | 1/51 | N/A | Nil | N/A | 2/4,300 |
| c.1219C>T | 11 | p.Arg407* | Nil | N/A | 1/144 | N/A | 0/4,300 |
| c.1513G>T | 13 | p.Glu505* | Nil | N/A | 1/144 | N/A | 0/4,300 |
| *Validation Phase 1, whole gene sequencing of RECQL in high-risk BC cases by Sanger sequencing* | | | | | | | |
| c.634C>T | 6 | p.Arg215* | 2/475 | N/A | Nil | N/A | 1/4,300 |
| c.1667_1667+3delAGTA | 13 | p.K555delinsMYKLIHYSFR | Nil | N/A | 2/475 | N/A | 0/4,300 |
| *Validation Phase 2, targeted genotyping of recurrent RECQL variants in BC cases and population controls* | | | | | | | |
| c.634C>T | 6 | p.Arg215* | 5/538 | 1/7,136 | N/A | N/A | 1/4,300 |
| c.1667_1667+3delAGTA | 13 | p.K555delinsMYKLIHYSFR | N/A | N/A | 30/13,136 | 2/4,702 | 0/4,300 |

\* Nucleotide positions are based on NM_002907.3 transcript of *RECQL*.

‡ Frequencies are for the European-American population of the NHLBI exome database.

Nil = not observed

FC = French Canadian

FIG. 5

| DNA Mutation* | Protein Change | Exon | Carrier Frequency | | Frequency among NHLBI Exome Data+ | C Score† |
|---|---|---|---|---|---|---|
| | | | Polish | FC | | |
| c.386G>A | p.Cys129Tyr | 4 | 1 | 0 | 1/4,300 | 22.5 |
| c.401C>T | p.Thr134Ile | 5 | 1 | 0 | 6/4,296 | 25 |
| c.518T>A | p.Val173Asp | 6 | 0 | 1 | 3/4,300 | 22 |
| c.610C>A | p.Leu204Ile | 6 | 1 | 0 | 0/4,300 | 19.57 |
| c.678G>T | p.Gln226His | 6 | 0 | 1 | 0/4,300 | 12.67 |
| c.760A>G | p.Thr254Ala | 7 | 1 | 0 | 0/4,300 | 16.19 |
| c.821G>A | p.Cys274Tyr | 7 | 1 | 0 | 0/4,300 | 15.19 |
| c.889A>G | p.Thr297Ala | 8 | 0 | 1 | 1/4,298 | 4.754 |
| c.898T>A | p.Phe300Ile | 8 | 7 | 0 | 4/4,299 | 12.57 |
| c.1042T>A | p.Leu348Met | 9 | 0 | 1 | 0/4,300 | 2.814 |
| c.1364G>A | p.Arg455His | 12 | 0 | 1 | 0/4,300 | 35 |
| c.1483G>C | p.Asp495His | 13 | 1 | 3 | 42/4,300 | 16.05 |
| c.1656G>T | p.Gln552His | 13 | 0 | 1 | 0/4,300 | 13.61 |
| c.1742A>G | p.Asn581Ser | 14 | 1 | 0 | 0/4,300 | 8.525 |

* Nucleotide positions are based on NM_002907.3 transcript of RECQL.

+ Exome Variant Server, NHLBI GO Exome Sequencing Project (ESP), Seattle, WA (URL: http://evs.gs.washington.edu/EVS/) [July 2014]

† C scores are calculated by Combined Annotation Dependent Depletion (CADD) algorithm (Kircher et al., 2014)

FC = French Canadian

FIG. 6

| Characteristic | RECQL Mutation Positive (n = 32) | | RECQL Mutation Negative (n = 13,579) | | P+ |
|---|---|---|---|---|---|
| | No./Total No. | % | No./Total No. | % | |
| Age, years | | | | | |
| Mean | 54.5 | | 53.2 | | |
| 18-30 | 0/32 | 0.0 | 176/13,579 | 1.3 | 0.5 |
| 31-40 | 1/32 | 3.1 | 1,295/13,579 | 9.5 | 0.3 |
| 41-50 | 16/32 | 50.0 | 5,485/13,579 | 40.4 | 0.3 |
| > 50 | 15/32 | 46.9 | 6,623/13,579 | 48.8 | 1.0 |
| Histology | | | | | |
| Ductal, grade 3 | 4/29 | 13.8 | 2,137/10,496 | 20.4 | 0.5 |
| Ductal, grade 1-2 | 12/29 | 41.4 | 4,423/10,496 | 42.1 | 0.9 |
| Ductal, grade unknown | 3/29 | 10.3 | 756/10,496 | 7.2 | 0.8 |
| Medullary | 1/29 | 3.4 | 287/10,496 | 2.7 | 0.8 |
| Lobular | 5/29 | 17.2 | 1,412/10,496 | 13.5 | 0.7 |
| Tubulolobular | 1/29 | 3.4 | 149/10,496 | 1.4 | 0.9 |
| DCIS | 1/29 | 3.4 | 357/10,496 | 3.4 | 1.0 |
| Other | 2/29 | 6.9 | 975/10,496 | 9.3 | 0.9 |
| ER positive | 22/29 | 75.9 | 6,987/9,839 | 71.0 | 0.7 |
| PR positive | 19/29 | 65.5 | 6,913/9,403 | 73.5 | 0.4 |
| Her2 positive | 4/24 | 16.7 | 1,421/7,729 | 18.4 | 0.8 |
| Size, cm | | | | | |
| < 1 | 2/27 | 7.4 | 1,153/9,042 | 12.7 | 0.6 |
| 1-1.9 | 15/27 | 55.5 | 3,578/9,042 | 39.6 | 0.1 |
| 2-4.9 | 10/27 | 37.0 | 3,898/9,042 | 43.1 | 0.6 |
| ≥ 5 | 0/27 | 0.0 | 413/9,042 | 4.6 | 0.5 |
| Lymph node positive | 14/27 | 51.8 | 4,060/9,015 | 45.0 | 0.6 |
| Multicentric | 3/27 | 11.1 | 1,237/9,061 | 13.6 | 0.9 |
| Bilateral | 1/31 | 3.2 | 424/10,990 | 3.8 | 0.8 |
| Neoadjuvant chemioterapy | 3/29 | 10.3 | 1,998/10,253 | 19.5 | 0.3 |
| Positive family history of breast cancer* | 9/31 | 29.0 | 1,831/11,477 | 15.9 | 0.08 |
| No. of relatives with breast cancer | | | | | |
| 1 | 6/31 | 19.3 | 1,502/11477 | 13.1 | 0.4 |
| ≥ 2 | 3/31 | 9.7 | 329/11477 | 2.9 | 0.08 |

* Family history refers to a first- or second-degree relative affected by breast cancer.

+ P value refers to comparison of *mutation*-positive vs. *mutation*-negative patients using Fisher's exact test.

Abbreviations: DCIS, ductal carcinoma *in situ*; ER, estrogen receptor; PR, progesterone receptor; Her2, human epidermal growth factor receptor 2.

FIG. 7

| | Breast cancer cases (n=13611) Mean age: 53.2 years Age range: 18-92 years | | Controls (n=4702) Mean age: 53.0 years Age range: 18-95 years | |
|---|---|---|---|---|
| Region | City | Mutation Frequency | City | Mutation Frequency |
| Northwestern Poland | Szczecin, Koszalin | 0.26% (11/4,152) | Szczecin, Koszalin | 0.04% (1/2,290) |
| Northeastern Poland | Olsztyn, Białystok | 0.15% (3/2,033) | Olsztyn, Białystok | 0.00% (0/405) |
| Central Poland | Bydgoszcz, Toruń Poznań, Warszawa Łódź, Zielona Góra | 0.19% (4/2,059) | Bydgoszcz, Toruń Poznań, Warszawa Łódź, Zielona Góra | 0.00% (0/582) |
| Southwestern Poland | Opole, Bielsko-Biała Wrocław | 0.26% (7/2,720) | Opole, Bielsko-Biała Świdnica | 0.09% (1/1,134) |
| Southeastern Poland | Kielce, Kraków Lublin, Rzeszów Brzozów | 0.26% (7/2,647) | Kielce, Kraków | 0.00% (0/291) |
| All regions | | 0.24% (32/13,611) | | 0.04% (2/4,702) |

BREAST CANCER BIOMARKERS AND METHODS OF USING SAME

RELATED APPLICATION

This application claims priority from, and the benefit of, U.S. Provisional Patent Application Ser. No. 62/138,874, filed on Mar. 26, 2015, the entirety of which is hereby incorporated by reference.

FIELD OF INVENTION

This invention relates to breast cancer markers, kits and methods for determining the susceptibility of a subject to developing breast cancer, and kits and methods for detecting, diagnosing, treating, and predicting responses to treatment for breast cancer.

BACKGROUND

The risk of breast cancer ("BC") varies between women, and genetic susceptibility plays an important role in the etiology of the disease; highly-penetrant alleles are estimated to account for up to 10% of all BC [1]. Two major breast cancer susceptibility genes, BRCA1 and BRCA2, were identified in the 1990s; they are responsible for ~15% to 20% of inherited BC [1-3]. Since then, other genes, such as ATM, CHEK2, NBN, PALB2, PTEN, and TP53, have been identified [4-9]. Together, all known breast cancer susceptibility genes are estimated to account for one-half of hereditary BC cases [1]. The genes responsible for the remaining ~50% are yet to be determined. Accordingly, there remains a need to identify further prognostic and diagnostic markers for breast cancer and to develop methods for determining a subject's susceptibility to breast cancer.

In genetically homogenous populations, seemingly unrelated affected individuals may, in fact, be distantly related and may share a mutant susceptibility allele inherited from a common ancestor. In these situations, by using highly parallel DNA sequencing methods, it is possible to look for associations with specific (causative) alleles, rather than to use linked genetic markers or to identify and sum multiple genetic variants at a single gene locus. Currently, exome sequencing facilitates the determination of all variants in an individual's genome coding regions through comparison to the reference sequence. Exome sequencing was first used successfully in 2009 to identify the gene mutation underlying Miller syndrome [17] and since then it has been employed to detect many other Mendelian rare genetic disorders. However, it has been less successful in identifying genes underlying complex disorders, like cancer.

SUMMARY

The inventor identified RECQL as a candidate BC susceptibility gene by whole exome sequencing ("WES") selected cases in two founder populations. The inventor's results suggest that truncating germ-line mutations in RECQL are associated with a significantly increased risk for breast cancer. The identification of recurrent mutations in two founder populations prompted the inventor to further investigate the association of RECQL with BC in two large samples of cases and controls in an efficient and cost-effective manner. This founder-based approach is likely to be successful in the search for other rarely-mutated cancer susceptibility genes.

In one aspect, the present invention provides a method for predicting a subject's risk of developing breast cancer. The method includes analyzing a diagnostic sample of the subject for the presence of at least one mutation in the RECQL gene. Detection of the presence of at least one RECQL mutation in the diagnostic sample can be indicative of at least a five-fold increase in risk of developing breast cancer as compared to an individual without at least one RECQL mutation. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein, including, without limitation, p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the nucleic acid includes genomic DNA, mRNA, or cDNA obtained from mRNA. In some embodiments, the step of analyzing the sample further includes obtaining the sample from the subject. In some embodiments, the step of determining the presence of the at least one mutation includes use of a PCR-based detection method and/or a hybridization-based method.

In another aspect, the invention provides a method for treating breast cancer in a subject. The method includes analyzing a diagnostic sample of the subject for the presence of at least one mutation in the RECQL gene and treating the subject when the presence of at least one mutation in the RECQL gene is detected. In some embodiments, the treatment includes administration of a TOP1 inhibitor (e.g., camptosar, hycamtin, and the like). In some embodiments, the treatment includes administration of a therapeutic agent that down-regulates the expression of the RECQL gene having at least one mutation. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of a PCR-based detection method and/or a hybridization-based method.

Another aspect of the present invention provides a method for assessing the prognosis of a subject having breast cancer. The method includes analyzing a diagnostic sample of the subject for the presence of at least one mutation in the RECQL gene. In some embodiments, detection of the presence of at least one RECQL mutation in the diagnostic sample is indicative of an unfavourable prognosis for the subject. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of a PCR-based detection method and/or a hybridization-based method.

In a further aspect, the present invention provides a method of determining whether a subject has breast cancer. The method includes analyzing a diagnostic sample of the subject for the presence of at least one mutation in the RECQL gene, and recommending a corroboration test for breast cancer if the at least one mutation is present in the diagnostic sample. In some embodiments, the corroboration test includes mammogram, ultrasound, magnetic resonance imaging, or biopsy. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of a PCR-based detection method and/or a hybridization-based method.

Another aspect of the present invention provides a method for developing a therapeutic agent useful in the treatment of breast cancer. The method includes screening for an agent that inhibits or down-regulates the expression of a RECQL gene having at least one mutation or the function of a protein expressed from the RECQL gene having at least one mutation. In some embodiments, the agent includes interference RNA. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of at least one of a PCR-based detection method and a hybridization-based method.

In another aspect, the present invention provides a method for reducing the risk of developing breast cancer in a subject who was not previously diagnosed with breast cancer. The method includes analyzing a diagnostic sample of the subject for the presence of at least one mutation in the RECQL gene, and recommending a treatment option for breast cancer if the at least one mutation is present in the diagnostic sample. In some embodiments, the treatment option includes mastectomy or lumpectomy. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of at least one of a PCR-based detection method and a hybridization-based method.

Another aspect of the present invention provides a method of determining whether a diagnosed breast cancer is expected to progress to invasive breast cancer in a subject. The method includes analyzing a diagnostic sample of the subject for the presence of at least one mutation in the RECQL gene. In some embodiments, detection of the presence of at least one RECQL mutation in the diagnostic sample is indicative that the diagnosed breast cancer is expected to progress to invasive breast cancer in the subject. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of a PCR-based detection method and/or a hybridization-based method.

In a further aspect, the present invention provides a method for assessing the efficacy of therapy to treat breast cancer in a subject who has undergone or is undergoing breast cancer therapy. The method includes analyzing a diagnostic sample of the subject for the presence of a protein expressed from a RECQL gene having at least one mutation. In some embodiments, detection of the presence of the protein in the diagnostic sample is indicative of a need to continue breast cancer therapy. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of a PCR-based detection method and/or a hybridization-based method.

Another aspect of the present invention provides a method of determining whether a subject is susceptible to developing breast cancer. The method includes analyzing a diagnostic sample of the subject for the presence of at least one mutation in the RECQL gene. In some embodiments, detection of the presence of at least one RECQL mutation in the diagnostic sample is indicative that the subject has a higher susceptibility to developing breast cancer relative to a person with no RECQL mutation. In some embodiments, the at least one mutation includes a missense variant, truncating mutation, nonsense mutation, splicing site mutation, frame shift insertion or deletion, or start codon change mutation. In some embodiments, the at least one mutation in the RECQL gene includes c.1667_1667+3delAGTA or c.643C>T. In some embodiments, the at least one mutation causes a change in the amino acid sequence of the RECQL protein. In some embodiments, the change in the amino acid sequence of the RECQL protein includes p.Arg215Ter. In some embodiments, the change in the amino acid sequence causes a change in the secondary structure of the RECQL protein. In some embodiments, the change in the amino acid sequence includes a displacement of amino acid residues for forming a β-hairpin in the RECQL protein. In some embodiments, the change in the amino acid sequence includes a deletion of lysine at codon 555 and an insertion of the amino acid sequence of SEQ ID NO:1 in the RECQL protein. In some embodiments, the step of analyzing the sample includes isolating nucleic acid from the sample; amplifying the isolated nucleic acid using primers that are specific for or capable of amplifying a sequence corresponding to the RECQL gene; and sequencing the amplified nucleic acid. In some embodiments, the step of analyzing the sample further includes obtaining the sample from the subject. In some embodiments, the nucleic acid includes genomic DNA, mRNA, or cDNA obtained from mRNA. In some embodiments, the step of determining the presence of the at least one mutation includes use of at least one of a PCR-based detection method and a hybridization-based method.

In another aspect, the present invention provides a mutated RECQL gene, a mutated RECQL protein, kits and agents for detecting these mutants, and use of the mutants, kits, and agents to determine a subject's susceptibility to developing breast cancer, or to detect, diagnose, treat, or predict response to treatment for breast cancer. For example, in one embodiment, the invention provides a use of an oligonucleotide capable of identifying at least one mutation in a RECQL gene to determine a subject's susceptibility to developing breast cancer. In some embodiments, the oligonucleotide includes a DNA or RNA probe. In some embodiments, the oligonucleotide is labelled with a detectable marker. In some embodiments, the detectable marker includes a radioactive marker or fluorescent marker. In some embodiments, the at least one mutation includes c.1667_1667+3delAGTA or c.643C>T.

In the foregoing aspects of the present invention, the breast cancer includes invasive breast cancer.

In some aspects of the present invention, the subject is negative for a mutation in BRCA1, BRCA2, CHEK2, NBN, or PALB2. In some aspects of the present invention, the subject is positive for one or more mutations in one or more of BRCA1, BRCA2, CHEK2, NBN, and PALB2, or in a combination of any of the foregoing genes.

Additional aspects of the present invention will be apparent in view of the description which follows.

BRIEF DESCRIPTION OF THE FIGURES

The invention will now be described in relation to the drawings.

FIG. 4 shows the RECQL truncating mutations identified in Polish and French-Canadian breast cancer patients.

FIG. 5 shows the RECQL missense variants identified by sequencing in the discovery phase (WES) and validation phase 1 (Sanger) among 619 Polish and 526 French-Canadian familial breast cancer patients.

FIG. 6 shows the clinical characteristics of Polish breast cancer patients with RECQL c.1667_1667+3delAGTA mutation compared to non-carriers.

FIG. 7 shows geographical distribution of RECQL c.1667_1667+3delAGTA mutation among 13,611 women with breast cancer, and among 4,702 female cancer-free controls.

DETAILED DESCRIPTION OF THE INVENTION

Figure 1A:
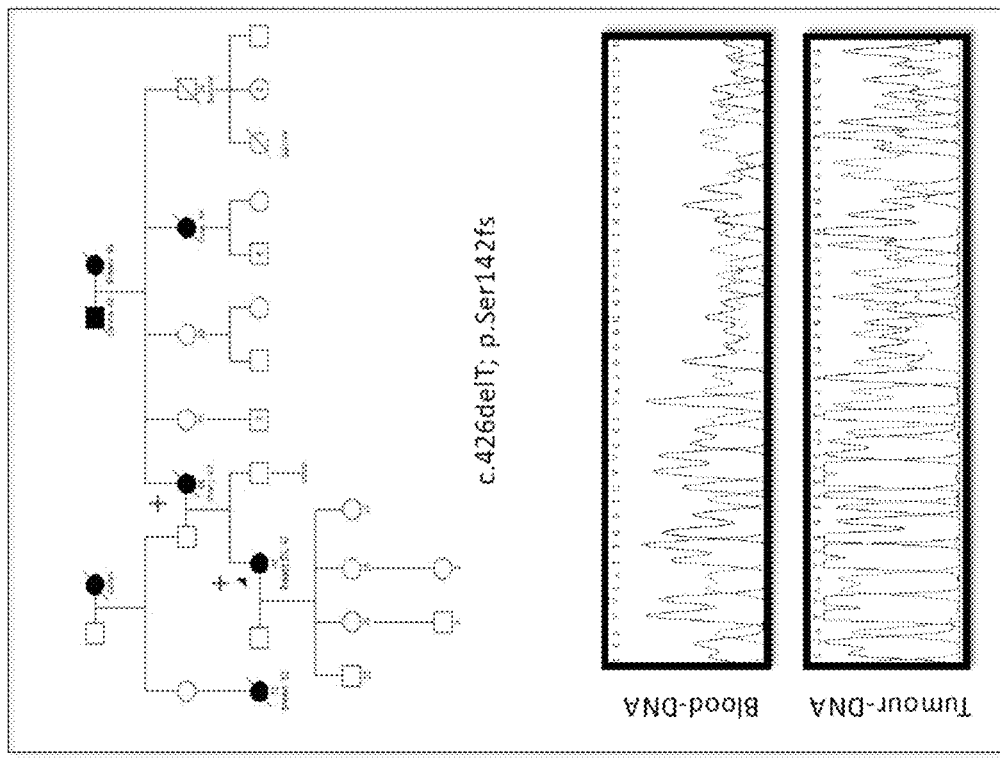
FIGS. 1A and 1B shows the pedigrees corresponding to two French-Canadian families, along with sequencing chromatopherograms of RECQL non-recurrent mutations identified during the discovery phase. (a) Pedigree, germline, and tumour chromatopherograms confirming the presence of c.132delGAAA; p.K45fs and the lack of loss of heterozygosity (LOH). (b) Pedigree, germline, and tumour chromatopherograms confirming the presence of c.426delT; p.Ser142fs and the lack of LOH.

To discover new breast cancer susceptibility genes, the inventor used two populations (Poland and Quebec, Canada) and applied whole exome sequencing in a discovery phase (n=195), followed by Sanger sequencing and TaqMan® and Sequenom® genotyping to validate these findings. The inventor identified rare recurrent RECQL mutations in each population. In Quebec, 7 of 1,013 higher-risk breast cancer cases and 1 of 7,136 newborns carried the c.634C>T (p.Arg215Ter) variant (p=0.00004). In Poland, 30 of 13,136 unselected breast cancer cases and 2 of 4,702 controls carried the c.1667_1667+3delAGTA, p.K555delinsMYKLIHYSFR variant (p=0.008). The relative risks associated with the two mutations were similar in that they increased the risk of breast cancer by 11- and 13-fold among familial cases in Poland and Quebec, respectively, and 5-fold among unselected cases in Poland.

RECQL is implicated in resolving stalled DNA replication forks to prevent double-stranded DNA breaks (dsDNA); this function is related to that of other known breast cancer genes, many of which are involved in repairing dsDNA breaks. The inventor concludes that RECQL is a breast cancer susceptibility gene. Accordingly, as discussed in greater detail below, this invention relates to breast cancer markers, methods of determining the susceptibility of a subject to developing breast cancer, and methods for detecting, diagnosing, treating, and predicting responses to treatment for breast cancer.

The following definitions are presented as an aid to understand the invention.

The terms "sample", "biological sample", "diagnostic sample", and the like refer to a material known or suspected of expressing or containing one or more polynucleotide or polypeptide cancer markers. The diagnostic sample may be any tissue (e.g., blood, bone, brain tissue, endometrial tissue, kidney tissue, mammary tissue, muscle tissue, nervous tissue, soft tissue, etc.), and may be removed by standard biopsy. Exemplary tissues for use in methods described herein include, without limitation, mammary gland tissue and endometrial tissue. The diagnostic sample may also be a bodily fluid, including, without limitation, cerebrospinal fluid, pericardial fluid, peritoneal fluid, saliva, serum, and urine.

The terms "polynucleotide" and "nucleic acid", used interchangeably herein, include polynucleotides that encode a native-sequence polypeptide, a polypeptide variant, a portion of a polypeptide, a chimeric polypeptide, or an isoform, precursor, complex, modified form, or derivative of any of the foregoing, and any precursors thereof. Polynucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may be modified after synthesis (e.g., by conjugation with a label, such as a radioactive, chemiluminescent, chemiflourescent, or fluorescent label, and the like). Other types of modifications to polynucleotides known to a person skilled in the art include substitution of one or more naturally-occurring nucleotides with an analog, internucleotide modifications (e.g., uncharged linkages, charged linkages), and the like.

"Oligonucleotides" include short, single-stranded polynucleotides that are at least seven nucleotides in length and less than about 250 nucleotides in length. The term "polynucleotides" includes oligonucleotides.

"Label" refers to a detectable compound or composition and "labelling" refers to the conjugation, fusion, or attachment of a detectable compound or composition to another. In some aspects described herein, the label is conjugated or fused directly or indirectly to a reagent, such as a polynucleotide probe or an antibody, and assists with the detection of the reagent to which it is conjugated or fused. The label itself can also be detectable (such as radioisotope labels or fluorescent labels and the like). In some aspects described herein, the label is an enzymatic label which catalyzes chemical alteration of a substrate compound or composition and results in a detectable product.

As used herein, the term "antibody" broadly includes all different types of antibody structures, such as monoclonal antibodies, polyclonal antibodies, multispecific antibodies (including bispecific antibodies), chimeric antibodies, humanized antibodies, fragments having antigen-binding activity, etc. The antibody can be produced by techniques well known to those skilled in the art. Polyclonal antibody, for example, can be produced by immunizing a mouse, rabbit, or rat with purified RECQL. Monoclonal antibody can then be produced by removing the spleen from the immunized mouse, and fusing the spleen cells with myeloma cells to form a hybridoma which, when grown in culture, will produce a monoclonal antibody.

The term "chimeric" refers to an antibody in which a portion of the heavy and/or light chain is derived from a particular source or species, while the remainder of the heavy and/or light chain is derived from a different source or species.

The term "diagnosis", as used herein, refers to the identification or classification of a molecular or pathological state, disease, or condition (e.g., cancer, a particular type of cancer, etc.). "Diagnosis" also refers herein to the classification of a particular subtype of cancer, such as by histopathological criteria or by molecular features (including a subtype characterized by expression of one or a combination of biomarkers, such as particular genes or proteins encoded by the genes).

"Mutation", with reference to a gene, means a mutation in the DNA sequence of the gene. Mutation may include a truncating mutation, splicing site mutation, frame shift insertion or deletion, missense mutation, nonsense mutation, start codon change mutation, intronic splicing mutation, or large rearrangement that includes deletion or duplication of the whole gene or part of the gene. Mutation includes polymorphisms, including single nucleotide polymorphisms. In some aspects described herein, mutation in a gene causes a change in the amino acid of the protein encoded by the gene.

"Mutation", with reference to a protein, means a protein having a changed amino acid sequence as a result of a mutation in the nucleic acid encoding the protein. The change in amino acid sequence of a protein may cause a change in the secondary structure of the protein. In some aspects described herein, the change in amino acid sequence displaces amino acid residues involved in protein folding or protein structure, such as a β-hairpin and the like. By way of example, the folding of a protein can be modified by the change in amino acid sequence.

"Primer" includes single-stranded polynucleotide that is capable of hybridizing to nucleic acid and allowing the polymerization of a complementary nucleic acid, generally by providing a free 3'-OH group.

"Vector" or "expression vector" refers to a nucleic acid molecule that is capable of propagating another nucleic acid to which it is linked. It includes vectors as self-replicating nucleic acid structures, vectors that incorporate into genomes of host cells to which the vectors are introduced, and vectors that can direct expression of nucleic acids to which vectors are linked.

"Marker" or "biomarker" refers to an indicator which can be detected in a sample, and includes predictive, diagnostic, and prognostic indicators and the like. The marker can be an indicator of a particular disease or disorder (e.g., breast cancer or other cancer) having certain molecular, pathological, histological, and/or clinical features. In some aspects described herein, the marker is a gene or a variation (including a mutation and/or polymorphism) of a gene. Exemplary biomarkers include, without limitation, polynucleotides, polypeptides, polypeptide and polynucleotide modifications (such as post-translational modifications and the like), carbohydrates, and/or glycolipid-based molecular markers. The "presence", "amount", or "level" of a marker associated with an increased clinical benefit to an individual is a detectable level of the marker in a sample. The presence, amount, or level of a marker can be measured by methods known to a person skilled in the art. The presence, amount, or level of a marker may be measured prior to treatment, during treatment, after treatment, or a combination of any of the foregoing.

"Cancer" refers to a proliferation of tumor cells in tissue having the unique trait of loss of normal controls, resulting in unregulated growth, lack of differentiation, local tissue invasion, and/or metastasis, and includes malignant tumors that are either invasive or non-invasive.

"Encode" refers to a polynucleotide "encoding" a polypeptide if, in its native state or when manipulated by methods well known to those skilled in the art, it can be transcribed and/or translated to produce the mRNA for the polypeptide and/or the polypeptide (or a fragment thereof). The anti-sense strand is the complement of such a nucleic acid, and the encoding sequence can be deduced therefrom.

"Array" or "microarray" refers to an ordered arrangement of hybridizable array elements on a substrate, such as solid substrate (e.g., glass slide and the like) or a semi-solid substrate (e.g., nitrocellulose membrane and the like). In some embodiments, the array elements may be polynucleotide probes (e.g. oligonucleotide). Array may include DNA microarrays (including cDNA microarrays, oligonucleotide microarrays, SNP microarrays, etc.), protein microarrays, peptide microarrays, antibody microarrays, and the like.

"Amplification" or "amplifying" refers to the production of one or more copies of a reference nucleic acid sequence or its complement. Amplification may be linear or exponential (e.g., in a polymerase chain reaction (PCR)). A nucleic acid copy produced from amplification may not have perfect sequence complementarity or identity relative to the reference sequence. In some embodiments, the copies can include nucleotide analogs, including deoxyinosine, intentional sequence alterations (such as alterations introduced through a primer that is hybridizable, but not fully complementary, to the template), and/or sequence errors that occur during the amplification process.

The terms "expression" and "expression level", in general, are used interchangeably and generally refer to the amount of a marker in a sample. "Expression" generally refers to the process by which information (e.g., gene-encoded and/or epigenetic) is converted into the structures present and operating in the cell. Therefore, as used herein, "expression" can refer to transcription into a polynucleotide (such as mRNA and the like), translation into a polypeptide, or even polynucleotide and/or polypeptide modifications (e.g., post-translational modification of a polypeptide and the like). Fragments of the transcribed polynucleotide, the translated polypeptide, or polynucleotide and/or polypeptide modifications (such as post-translational modification of a polypeptide and the like) will also be regarded as expressed whether they originate from a transcript generated by alternative splicing or a degraded transcript, or from a post-translational processing of the polypeptide (e.g., by proteolysis). "Expressed genes" include those that are transcribed into a polynucleotide as mRNA and then translated into a polypeptide, and also those that are transcribed into RNA but not translated into a polypeptide (such as transfer and ribosomal RNAs and the like).

An "isolated" nucleic acid refers to a nucleic acid molecule that has been separated from a component of its natural environment. An isolated nucleic acid includes a nucleic acid molecule contained in cells that ordinarily contain the nucleic acid molecule. The nucleic acid molecule may be present extrachromosomally or at a chromosomal location that is different from its natural location.

An "isolated" antibody is an antibody which has been separated from a component of its natural environment. In some aspects described herein, an antibody is purified to greater than 95% or 99% purity as determined by methods known to a person skilled in the art, such as electrophoretic methods (e.g., SDS-PAGE, isoelectric focusing, capillary electrophoresis), chromatographic methods (e.g., ion exchange chromatography or reverse phase HPLC), and/or the like.

The term "treatment", "treat", or "treating" refers to clinical intervention in an attempt to alter the natural course of the individual being treated, and can be performed either for prophylaxis or during the course of clinical pathology. Effects of treatment can include preventing occurrence or recurrence of disease, alleviating symptoms, diminishing any direct or indirect pathological consequences of disease, preventing metastasis, decreasing the rate of disease progression, ameliorating the disease state, minimizing the clinical impairment or symptoms resulting from the disease, diminishing any pain or discomfort suffered by the subject, remission or improved prognosis, and extending the survival of a subject beyond that which would otherwise be expected in the absence of such treatment. With reference to cancer, treatment also includes inhibiting or preventing the development or spread of the cancerous cells or by limiting, suspending, terminating, or otherwise controlling the maturation and proliferation of cells involved in the cancer. As used herein, "treatment" includes therapy.

The term "sequencing" and its variants include obtaining sequence information from a strand of a nucleic acid molecule, typically by determining the identity of at least some nucleotides (including their nucleobase components) within the nucleic acid molecule. The term sequencing may also refer to determining the order of nucleotides (base sequences) in a nucleic acid sample (e.g. DNA or RNA). Many techniques are available and known to a person skilled in the art, such as Sanger sequencing, high-throughput sequencing technologies (such as the GS FLX platform offered by Roche Applied Science, Penzberg, Germany, based on pyro sequencing), and the like. High-throughput sequencing technologies refer to sequencing technologies having increased throughput as compared to traditional Sanger- and capillary-electrophoresis-based approaches (e.g., with the ability to generate hundreds of thousands or millions of relatively small sequence reads at a time). These high-through-put sequencing technologies include, but are not limited to, sequencing by synthesis, sequencing by ligation, pyrosequencing, sequencing by hybridization, and/or the like.

The term "exome" refers to the collection of genomic segments that include protein coding regions, exons, promoters, known ncRNAs (non-coding RNAs), and UTRs. The exome comprises about 2% of the human genome.

The term "whole exome sequencing" refers to selective sequencing of coding regions of the DNA genome. The targeted exome is usually the portion of the DNA that translates into proteins, although regions of the exome that do not translate into proteins can also be included within the sequence.

As described herein, the inventor has identified mutations in the RECQL gene that are associated with breast cancer susceptibility. These findings identify a breast cancer biomarker for use in diagnosing, preventing, and monitoring breast cancer.

Unless otherwise indicated, "RECQL" includes a RECQL protein, a "RECQL analogue", and a "RECQL mutant". As used herein, the "RECQL protein" has the amino acid sequence corresponding to Genbank accession number NC_000012. A "RECQL analogue", as used herein, is a functional variant of the RECQL protein, having RECQL biological activity, that has 60% or greater (e.g., 70% or greater) amino-acid-sequence homology with the RECQL protein. A "RECQL analogue" includes a variant of the RECQL protein that has a homologous three-dimensional conformation. As further used herein, the expression "RECQL biological activity" includes helicase function and/or protein binding to DNA and other proteins. The term "RECQL mutant" includes RECQL protein encoded by a RECQL gene having a mutation. A RECQL mutant can have differences functionally and/or structurally from a RECQL protein. RECQL, RECQL analogues, and RECQL mutants can be produced synthetically or recombinantly, or can be isolated from native cells. For example, RECQL can be produced recombinantly, using conventional techniques and cDNA encoding RECQL (Genbank accession number NC_000012).

In the methods described herein, protein to be assayed can be isolated and purified from a diagnostic sample using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody to RECQL), and precipitation (e.g., with isopropanol and a reagent such as Trizol). Isolation and purification of a protein can be followed by electrophoresis (e.g., on an SDS-polyacrylamide gel). Nucleic acid can be isolated from a diagnostic sample using standard techniques known to one of skill in the art.

In accordance with a method of the present invention, the presence of a mutation in the RECQL gene in a subject, individual, or patient can be diagnosed by assaying a diagnostic sample of the subject, individual, or patient for the presence of the RECQL gene having a mutation and/or the expression of a RECQL polypeptide encoded by a RECQL gene having a mutation (a RECQL mutant). The subject, individual, or patient is preferably a human. In some embodiments, the subject is a mammal having helicases similar to RECQL. A subject, individual, or patient can be afflicted with or suspected of having or being pre-disposed to breast cancer, as described herein. In some cases, the subject, individual, or patient is negative for a mutation in BRCA1, BRCA2, CHEK2, NBN, or PALB2. However, in other cases, the subject, individual, or patient has one or more mutations in BRCA1, BRCA2, CHEK2, NBN, PALB2, or a combination of any of the foregoing genes. A diagnostic sample of the subject, individual, or patient can be assayed for RECQL mutant expression by assaying for RECQL protein (as defined above), RECQL cDNA, or RECQL mRNA. The appropriate form of RECQL will be apparent based on the particular techniques discussed herein.

Quantities of RECQL mutant expression can be determined using a standard assay for quantification, such as flow cytometry, Western blot analysis, or an ELISA for measuring protein quantities, as described below. For example, an ELISA can be run on each sample in duplicate, and the means and standard deviations of the quantity of the RECQL protein can be determined.

A diagnostic sample of a subject can be assayed for a RECQL gene having a mutation and/or for the expression of such gene (RECQL mutant expression), using assays and detection methods readily determined from the known art, including, without limitation, immunological techniques, hybridization analysis, fluorescence imaging techniques, and/or radiation detection. For example, according to an aspect of the present invention, a diagnostic sample of the subject can be assayed for RECQL mutant expression using an agent reactive with RECQL protein or RECQL nucleic acid.

As used herein, "reactive" means the agent has affinity for, binds to, or is directed against RECQL protein or RECQL nucleic acid. As further used herein, an "agent" includes a protein, polypeptide, peptide, nucleic acid (including DNA or RNA), antibody, Fab fragment, F(ab')2 fragment, molecule, compound, antibiotic, drug, and any combinations thereof. A Fab fragment is a univalent antigen-binding fragment of an antibody, which is produced by papain digestion. A F(ab')2 fragment is a divalent antigen-binding fragment of an antibody, which is produced by pepsin digestion. By way of example, the agent of the present invention can be labeled with a detectable marker. Agents that are reactive with RECQL protein or nucleic acid can be identified by contacting RECQL protein or nucleic acid with an agent of interest and assessing the ability of the agent to bind to the RECQL protein or RECQL nucleic acid.

In one embodiment of the present invention, the agent reactive with RECQL is an antibody. Antibodies for use herein can be labeled with a detectable marker. Labeling of an antibody can be accomplished using one of a variety of labeling techniques, including peroxidase, chemiluminescent labels known in the art, and radioactive labels known in the art. The detectable marker of the present invention can be, for example, a nonradioactive or fluorescent marker, such as biotin, fluorescein (FITC), acridine, cholesterol, or carboxy-X-rhodamine (ROX), which can be detected using fluorescence and other imaging techniques readily known in the art. Alternatively, the detectable marker can be a radioactive marker, including, for example, a radioisotope. The radioisotope can be any isotope that emits detectable radiation, such as 35S, 32P, or 3H. Radioactivity emitted by the radioisotope can be detected by techniques well known in the art. For example, gamma emission from the radioisotope can be detected using gamma imaging techniques, particularly scintigraphic imaging. By way of example, the agent of the present invention is a high-affinity antibody labeled with a detectable marker.

Where the agent of the present invention is an antibody reactive with RECQL, a diagnostic sample taken from the subject can be purified by passage through an affinity column which contains the RECQL antibody as a ligand attached to a solid support, such as an insoluble organic polymer in the form of a bead, gel, or plate. The antibody attached to the solid support can be used in the form of a column. Examples of suitable solid supports include, without limitation, agarose, cellulose, dextran, polyacrylamide, polystyrene, sepharose, and other insoluble organic polymers. The RECQL antibody can be further attached to the solid support through a spacer molecule, if desired. Appropriate binding conditions (e.g., temperature, pH, and salt concentration) can be readily determined by the skilled artisan. By way of example, the RECQL antibody can be attached to a sepharose column, such as Sepharose 4B.

Where the agent is an antibody, a diagnostic sample of the subject can be assayed for RECQL mutant expression using binding studies that utilize one or more antibodies immunoreactive with RECQL mutant, along with standard immunological detection techniques. For example, the RECQL mutant eluted from the affinity column can be subjected to an ELISA assay, Western blot analysis, flow cytometry, or any other immunostaining method employing an antigen-antibody interaction. For example, the diagnostic sample can be assayed for RECQL mutant expression using Western blotting.

Alternatively, a diagnostic sample of a subject can be assayed using hybridization analysis of nucleic acid extracted from the diagnostic sample taken from the subject to determine the presence of a mutation in the RECQL gene. In this aspect of the invention, the hybridization analysis can be conducted using Northern blot analysis of mRNA. This method also can be conducted by performing a Southern blot analysis of DNA using at least one nucleic acid probe which hybridizes to nucleic acid encoding RECQL. The nucleic acid probes of the present invention can be prepared by a variety of techniques known to those skilled in the art, including, without limitation, the following: restriction enzyme digestion of RECQL nucleic acid; and automated synthesis of oligonucleotides having sequences which correspond to selected portions of the nucleotide sequence of the RECQL nucleic acid, using commercially-available oligonucleotide synthesizers.

The nucleic acid probes used herein can be DNA or RNA, and can vary in length from about 8 nucleotides to the entire length of the RECQL nucleic acid. In some embodiments, the nucleic acid probes are oligonucleotides. The RECQL nucleic acid used in the probes can be derived from mammalian RECQL. The nucleotide sequence for human RECQL is known. Using this sequence as a probe, the skilled artisan could readily clone corresponding RECQL cDNA from other species. In addition, the nucleic acid probes of the present invention can be labeled with one or more detectable markers. Labeling of the nucleic acid probes can be accomplished using one of a number of methods known in the art (e.g., nick translation, end labeling, fill-in end labeling, polynucleotide kinase exchange reaction, random priming, SP6 polymerase (for riboprobe preparation)) along with one of a variety of labels (e.g., radioactive labels, such as 35S, 32P, or 3H, or nonradioactive labels, such as biotin, fluorescein (FITC), acridine, cholesterol, or carboxy-X-rhodamine (ROX)). Combinations of two or more nucleic acid probes (or primers), corresponding to different or overlapping regions of the RECQL nucleic acid, also can be used to assay a diagnostic sample for a mutation in the RECQL gene, using, for example, PCR or RT-PCR. In some embodiments, these nucleic acid probes are used in an array or microarray.

The detection of RECQL mutant expression in methods of the present invention can be followed by an assay to measure or quantify the extent of RECQL mutant expression in a diagnostic sample of a subject. Such assays are well known to one of skill in the art, and can include immunohistochemistry/immunocytochemistry, flow cytometry, mass spectroscopy, Western blot analysis, or an ELISA for measuring amounts of RECQL protein. For example, to use an immunohistochemistry assay, histological (paraffin-embedded) sections of tissue can be placed on slides, and then incubated with an antibody against RECQL. The slides can then be incubated with a second antibody (against the primary antibody), which is tagged to a dye or other colorimetric system (e.g., a fluorochrome, a radioactive agent, or an agent having high electron-scanning capacity), to permit visualization of RECQL that is present in the sections. In some embodiments, RECQL mutant expression can be detected using arrays, including antibody arrays and the like.

It is contemplated that a diagnostic sample of the present invention frequently will be assayed for RECQL mutant expression not by the subject or patient, nor by the subject's or patient's consulting physician, but by a laboratory technician or other clinician. Accordingly, the method of the present invention can further include providing to a subject's or patient's consulting physician a report of the results obtained upon assaying a diagnostic sample of the subject or patient for RECQL mutant expression.

In other aspects, the present invention provides a method of predicting a subject's risk of developing breast cancer. The method includes analyzing a diagnostic sample of the subject for the presence of at least one mutation in the RECQL gene. The detection of the presence of at least one RECQL mutation in the diagnostic sample can be indicative of at least a five-fold increase in risk of developing breast cancer as compared to an individual without at least one RECQL mutation.

The prevent invention also provides a method for treating breast cancer in a subject. The method includes analyzing a diagnostic sample of the subject for the presence of at least one mutation in the RECQL gene and treating the subject when the presence of at least one mutation in the RECQL gene is detected. In some embodiments, the treatment comprises administering a DNA topoisomerase 1 (TOP1) inhibitor, such as camptostar, hycamtin, and the like. In some embodiments, the treatment comprises administering a therapeutic agent that down-regulates the expression of the RECQL gene having at least one mutation. In some embodiments, the treatment comprises administration of a combination of a TOP1 inhibitor and a down-regulator of expression of the RECQL gene having at least one mutation. In some embodiments, the treatment comprises administering a therapeutic agent in a therapeutically-effective amount. As used herein, a "therapeutically-effective amount" refers to an amount of a therapeutic agent effective, at dosages and for periods of time necessary, to achieve the desired therapeutic result. A therapeutically-effective amount of a therapeutic agent (including agonist, antagonist, and/or the like) can vary based on different factors, such as the disease state, age, sex, and weight of the subject, and the ability of the therapeutic agent to elicit a desired response in the subject. A therapeutically-effective amount is also one in which any toxic or detrimental effects of the substance/molecule, agonist, or antagonist are outweighed by the therapeutically-beneficial effects.

The present invention further provides a method for assessing the prognosis of a subject having breast cancer. The method comprises analyzing a diagnostic sample of the subject for the presence of at least one mutation in the RECQL gene. Detection of the presence of at least one RECQL mutation in the diagnostic sample is indicative of an unfavourable prognosis of the subject.

In addition, the present invention provides a method of determining whether a subject has breast cancer. The method includes analyzing a diagnostic sample of the subject for the presence of at least one mutation in the RECQL gene, and recommending a corroboration test for breast cancer if the at least one mutation is present in the diagnostic sample. In some embodiments, the corroboration test includes mammogram, ultrasound, magnetic resonance imaging, or biopsy, or a combination of more than one of any of the foregoing.

In another aspect, the present invention provides a method for developing a therapeutic agent useful in the treatment of breast cancer. The method includes screening for an agent that inhibits or down-regulates the expression of a RECQL gene having at least one mutation or the function of a protein expressed from the RECQL gene having at least one mutation. In some embodiments, the agent comprises interference RNA.

The present invention also provides a method for reducing the risk of developing breast cancer in a subject who has not previously been diagnosed with breast cancer. The method includes analyzing a diagnostic sample of the subject for the presence of at least one mutation in the RECQL gene, and recommending a treatment option for breast cancer if the at least one mutation is present in the diagnostic sample. In some embodiments, the treatment option comprises mastectomy or lumpectomy.

In a further aspect, the present invention provides a method of determining whether a diagnosed breast cancer is expected to progress to invasive breast cancer in a subject. The method includes analyzing a diagnostic sample of the subject for the presence of at least one mutation in the RECQL gene. The detection of the presence of at least one RECQL mutation in the diagnostic sample can be indicative that the diagnosed breast cancer is expected to progress to invasive breast cancer in the subject.

The present invention also provides a method of determining whether a subject is susceptible to developing breast cancer. The method includes analyzing a diagnostic sample of the subject for the presence of at least one mutation in the RECQL gene. Detection of the presence of at least one RECQL mutation in the diagnostic sample can be indicative that the subject has a higher susceptibility to developing breast cancer relative to a person with no RECQL mutation.

In the methods described herein, the step of analyzing a diagnostic sample can include obtaining the sample from the subject; isolating nucleic acid from the sample; amplifying the isolated nucleic acid using primers that are specific for or capable of amplifying a sequence corresponding to the RECQL gene; and sequencing the amplified nucleic acid. In some embodiments, the isolated nucleic acid includes genomic DNA, mRNA, and/or cDNA obtained from mRNA. In some embodiments, the step of determining the presence of the at least one mutation includes use of at least one of a PCR-based detection method and a hybridization-based method. In some embodiments, the step of determining the presence of the at least one mutation includes an immunohistochemical analysis. In some embodiments, an array or a microarray is used for identifying at least one mutation in the RECQL gene.

The present invention provides a method for assessing the efficacy of therapy to treat breast cancer in a subject or patient who has undergone or is undergoing breast cancer therapy. The method of the present invention includes assaying a diagnostic sample of the subject or patient for the RECQL gene having a mutation or the expression of RECQL encoded therefrom, wherein detection of the presence of the RECQL mutant is indicative of a need to continue therapy to treat the breast cancer.

The diagnostic sample can be assayed for expression of RECQL in vitro or in vivo. In addition, the diagnostic sample can be assayed for expression of RECQL using all of the various assays and methods of detection and quantification described above. This method of the present invention provides a means for monitoring the effectiveness of therapy to treat a breast cancer by permitting the periodic assessment of levels of RECQL mutant expression in a diagnostic sample taken from a subject or patient.

In accordance with this method, a diagnostic sample of a subject or patient can be assayed, and levels of RECQL mutant expression can be assessed, at any time following the initiation of therapy to treat breast cancer. For example, levels of RECQL mutant expression can be assessed while the subject or patient is still undergoing treatment for breast cancer. Where RECQL mutant expression is still detected at levels elevated above normal in an assayed diagnostic sample of the subject or patient, a physician can choose to continue with the subject's or patient's treatment for the breast cancer. Where levels of RECQL mutant expression in an assayed diagnostic sample of the subject or patient decrease through successive assessments, it can be an indication that the treatment for breast cancer is working, and that treatment doses could be decreased or even ceased. Where levels of RECQL mutant in an assayed diagnostic sample of the subject or patient do not rapidly decrease through successive assessments, it can be an indication that the treatment for breast cancer is not working, and that treatment doses could be increased. Where RECQL mutant expression is no longer detected at levels elevated above normal in an assayed diagnostic sample of a subject or patient, a physician can conclude that the treatment for breast cancer has been successful, and that such treatment can cease.

It is also within the confines of the present invention to assess levels of RECQL mutant expression following completion of the subject's or patient's treatment for breast cancer, in order to determine whether the breast cancer has recurred in the subject or patient. Accordingly, an assessment of levels of RECQL mutant expression in an assayed diagnostic sample can provide a convenient way to conduct follow-ups of patients with breast cancer. Furthermore, as described above, it is within the confines of the present invention to use assessed levels of RECQL mutant expression in an assayed diagnostic sample as a clinical or pathologic staging tool, as a means of determining the extent of the breast cancer in the subject or patient, and as a means of ascertaining appropriate treatment options. This method of the present invention further includes providing to a subject's or patient's consulting physician a report of the results obtained upon assaying a diagnostic sample of the subject or patient for RECQL mutant expression.

In another aspect, the present invention provides a method for assaying a diagnostic sample for RECQL mutant expression or the presence of a mutation in the RECQL gene. This affords a useful means of providing information concerning the prognosis of a subject or patient who has breast cancer. Accordingly, the present invention further provides a method for assessing the prognosis of a subject who has breast cancer, by assaying a diagnostic sample of the subject for RECQL mutant expression. The subject's prognosis improves with a decrease in RECQL mutant expression in the diagnostic sample, the subject's prognosis worsens with an increase in RECQL mutant expression in the diagnostic sample, the subject's prognosis is favorable at low levels of RECQL mutant expression in the diagnostic sample, and the subject's prognosis is unfavorable at high levels of RECQL mutant expression in the diagnostic sample.

The diagnostic sample can be assayed in vitro or in vivo. In addition, the diagnostic sample may be assayed using all of the various assays and detection and quantification methods described herein. This method of the present invention provides a means for determining the prognosis of a subject or patient diagnosed with breast cancer based upon the level of RECQL mutant expression in an assayed diagnostic sample of the subject or patient or the presence of a mutation in the RECQL gene.

In accordance with this method, a diagnostic sample of a subject or patient can be assayed, and levels of RECQL mutant expression or the presence of a mutation in the RECQL gene can be assessed, at any time during or following the diagnosis of breast cancer in the subject or patient. For example, levels of RECQL mutant expression or presence of in a mutation in RECQL gene in the assayed diagnostic sample can be assessed before the subject or patient undergoes treatment for breast cancer, in order to determine the subject's or patient's initial prognosis. If a mutation in the RECQL gene is identified, then the physician can recommend treatment options, such as mastectomy or lumpectomy. Similarly, levels of RECQL mutant expression or the presence of a mutation in the RECQL gene in an assayed diagnostic sample can be assessed while the subject or patient is undergoing treatment for breast cancer, in order to determine whether the subject's or patient's prognosis has become more or less favorable.

Where levels of RECQL mutant expression detected in an assayed diagnostic sample of the subject or patient are, or continue to remain, significantly high, a physician can conclude that the subject's or patient's prognosis is unfavorable. Where levels of RECQL mutant expression in an assayed diagnostic sample of the subject or patient decrease through successive assessments, it can be an indication that the subject's or patient's prognosis is improving. Where levels of RECQL mutant in an assayed diagnostic sample of the subject or patient do not decrease significantly through successive assessments, it can be an indication that the subject's or patient's prognosis is not improving. Where RECQL mutant expression is low, or is no longer detected in an assayed diagnostic sample of the subject or patient, a physician can conclude that the subject's or patient's prognosis is favorable. This method also includes providing to a subject's or patient's consulting physician a report of the results obtained upon assaying a diagnostic sample of the subject or patient for RECQL mutant expression.

The discovery that mutation in the RECQL gene is associated with elevated risks of breast cancer provides a means of identifying patients with increased risk of breast cancer, and presents the potential for commercial application in the form of a test for the diagnosis of breast cancer and kits including same. The development of such a test or kit would provide general screening procedures; these procedures could assist in the early detection and diagnosis of breast cancers, and could provide a method for the follow-up of patients in which a mutation in the RECQL gene is present. Accordingly, the present invention further provides a kit for use as an assay of breast cancer, comprising an agent reactive with RECQL mutant or for identifying a mutation in the RECQL gene. The agent can be any of those described above, and can be used in any of the above-described assays or methods for detecting or quantifying RECQL mutant expression.

It is also contemplated herein that a RECQL mutant, as identified by the inventor, can be inhibited. A RECQL mutant can be inhibited in a subject by disabling, disrupting, or inactivating the function of RECQL mutant in a tumor in the subject, or by diminishing the amount of RECQL mutant in a tumor in the subject. Furthermore, RECQL can be inhibited by targeting RECQL mutant directly, or by targeting a molecule that modulates or regulates RECQL mutant levels.

In one embodiment of the present invention, a RECQL mutant is inhibited by administering a RECQL mutant inhibitor to a subject who has breast cancer. As used herein, "a RECQL mutant inhibitor" includes a protein; a polypeptide; a peptide; a nucleic acid, including DNA, RNA, a ribozyme specific for RECQL mutant, and an oligonucleotide antisense to RECQL; an antibody, including a monoclonal and a polyclonal antibody, as described above, an antibody specific for RECQL exofacial epitopes, and an antibody specific for other RECQL epitopes; a Fab fragment, as described above; a F(ab')2 fragment, as described above; a molecule; a compound; an antibiotic; a drug; and any combinations thereof. Additionally, the RECQL mutant inhibitor of the present invention can be an agent reactive with RECQL mutant protein or nucleic acid, as defined above. The RECQL mutant inhibitor can partially or completely block, inhibit, or neutralize RECQL biological activity.

Oligonucleotides antisense to RECQL gene having a mutation can be designed based on the nucleotide sequence of the RECQL gene (Genbank accession number NC_000012). For example, a partial sequence of the RECQL nucleotide sequence (generally, 18-20 base pairs), or a variation sequence thereof, can be selected for the design of an antisense oligonucleotide. This portion of the RECQL nucleotide sequence can be within the 5' domain. A nucleotide sequence complementary to the selected partial sequence of the RECQL gene, or the selected variation sequence, can then be chemically synthesized using one of a variety of techniques known to those skilled in the art, including, without limitation, automated synthesis of oligonucleotides having sequences which correspond to a partial sequence of the RECQL nucleotide sequence, or a variation sequence thereof, using commercially-available oligonucleotide synthesizers.

Once the desired antisense oligonucleotide has been prepared, its ability to inhibit RECQL mutant can then be assayed. For example, the oligonucleotide antisense to a RECQL gene having a mutation can be contacted with tumor cells derived from a tumor cell line transfected with RECQL gene having a mutation, and the levels of RECQL mutant expression in the cells can be determined using standard techniques, such as Western blot analysis. Alternatively, the antisense oligonucleotide can be delivered to tumor cells derived from a tumor cell line transfected with RECQL gene having a mutation using a liposome vehicle, and the levels of RECQL mutant expression in the cells can then be determined using standard techniques, such as Western blot analysis. Where the level of RECQL mutant expression in tumor cells is reduced in the presence of the designed antisense oligonucleotide, it can be concluded that the oligonucleotide could be a useful RECQL mutant inhibitor.

It is within the confines of the present invention that an oligonucleotide antisense to RECQL gene having a mutation can be co-administered with another therapeutic agent, such as a topoisomerase I inhibitor (e.g., irinotecan, topotecan, camptothecin, or lamellarin D), in order to increase the effectiveness of the treatment, to increase the efficacy of targeting, and/or to increase the efficacy of treatment. Moreover, oligonucleotide antisense to RECQL gene having a mutation can be prepared using modified bases (e.g., a phosphorothioate) to make the oligonucleotide more stable and better able to withstand degradation.

The present invention also provides the use of an oligonucleotide capable of identifying at least one mutation in a RECQL gene to determine a subject's susceptibility to developing breast cancer. The oligonucleotide can be labelled with a detectable marker, such as a radioactive marker, fluorescent marker, the like, or a combination of any of the foregoing.

Agents reactive with RECQL mutant protein can act as antagonists or RECQL mutant inhibitors, thereby reducing the activity of RECQL mutants. Agents that are reactive with RECQL mutant nucleic acid can suppress expression of the RECQL mutant nucleic acid (e.g., by functioning as a repressor). Agents that are reactive with either RECQL mutant protein or nucleic acid can be identified using standard in vitro assays known in the art, including binding assays. For example, a candidate agent can be contacted with RECQL mutant protein or nucleic acid, and the ability of the agent to bind to the RECQL mutant protein or nucleic acid can be assessed using standard techniques.

Agents that regulate the expression of RECQL mutant nucleic acid, including agents that bind to sites that downregulate RECQL mutant, also can be useful as RECQL mutant inhibitors in the present invention. Accordingly, the RECQL mutant inhibitor of the present invention can be a modulator of RECQL mutant expression. The modulator can be a protein, polypeptide, peptide, nucleic acid (including DNA or RNA), antibody, Fab fragment, F(ab')2 fragment, molecule, compound, antibiotic, drug, or other agent, as defined herein, that terminates or downregulates RECQL mutant expression. Appropriate modulators of RECQL mutant expression can be identified by contacting a candidate agent with a cell transformed with a vector comprising the RECQL mutant nucleic acid, and assessing the effect of the agent on expression of RECQL mutant nucleic acid.

Once the candidate agent or modulator of the present invention has been screened, and has been determined to have a suitable inhibitory effect on RECQL mutant (i.e., it is reactive with RECQL mutant, it binds RECQL mutant, or it otherwise inactivates RECQL mutant), it can be evaluated for its effect on tumors and other defects in cell proliferation. In particular, the candidate agent or modulator can be assessed for its ability to act as an inhibitor to cell division or to otherwise function as an appropriate tumor-suppressing agent. It is expected that the RECQL mutant inhibitor of the present invention will be useful in treating breast cancer, including those disclosed herein, and in creating disease models.

In the method of the present invention, a RECQL mutant inhibitor is administered to a subject who has breast cancer to treat the breast cancer in the subject. In some embodiments, the RECQL mutant inhibitor is administered in a therapeutically-effective amount. The therapeutically effective amount of RECQL mutant inhibitor will vary depending on the particular factors of each case, including the type of breast cancer, the stage of the breast cancer, the subject's weight, the severity of the subject's condition, and the method of administration. These amounts can be readily determined by the skilled artisan.

In accordance with this method of the present invention, the RECQL mutant inhibitor can be administered to a subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump.

For oral administration, the formulation of the RECQL mutant inhibitor can be presented as capsules, tablets, powders, granules, or as a suspension. The formulation can have conventional additives, such as lactose, mannitol, corn starch, or potato starch. The formulation can also be presented with binders, such as crystalline cellulose, cellulose derivatives, acacia, corn starch, or gelatins. Additionally, the formulation can be presented with disintegrators, such as corn starch, potato starch, or sodium carboxymethylcellulose. The formulation can also be presented with dibasic calcium phosphate anhydrous or sodium starch glycolate. Finally, the formulation can be presented with lubricants, such as talc or magnesium stearate.

For parenteral administration, the RECQL mutant inhibitor can be combined with a sterile aqueous solution which is preferably isotonic with the blood of the subject. Such a formulation can be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations can be presented in unit or multi-dose containers, such as sealed ampules or vials. The formulation can be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the RECQL mutant inhibitor can be combined with skin penetration enhancers, such as propylene glycol, polyethylene glycol, isopropanol, ethanol, oleic acid, N-methylpyrrolidone, and the like, which increase the permeability of the skin to the RECQL mutant inhibitor, and permit the RECQL mutant inhibitor to penetrate through the skin and into the bloodstream. The RECQL mutant inhibitor/enhancer composition can also be further combined with a polymeric substance, such as ethylcellulose, hydroxypropyl cellulose, ethylene/vinylacetate, polyvinyl pyrrolidone, and the like, to provide the composition in gel form, which can be dissolved in solvent, such as methylene chloride, evaporated to the desired viscosity, and then applied to backing material to provide a patch. The RECQL mutant inhibitor can be administered transdermally, at or near the site on the subject where the breast cancer is localized. Alternatively, RECQL mutant inhibitor can be administered transdermally at a site other than the affected area, in order to achieve systemic administration.

The RECQL mutant inhibitor of the present invention can also be released or delivered from an osmotic mini-pump or other time-release device. The release rate from an elementary osmotic mini-pump can be modulated with a microporous, fast-response gel disposed in the release orifice. An osmotic mini-pump would be useful for controlling release, or targeting delivery, of the RECQL mutant inhibitor.

Where the RECQL mutant inhibitor is a protein, the RECQL mutant inhibitor protein can be administered to a subject by introducing to the subject the RECQL mutant inhibitor protein itself, or by introducing to the subject a nucleic acid encoding the RECQL mutant inhibitor in a manner permitting expression of the RECQL mutant inhibitor protein. The RECQL mutant inhibitor protein, and other RECQL mutant inhibitors, can be introduced to a subject by known techniques used for the introduction of proteins and other drugs, including, for example, injection and transfusion. Where the breast cancer is localized to a particular portion of the body of the subject, it may be desirable to introduce the RECQL mutant inhibitor directly to that area by injection or by some other means (e.g., by introducing RECQL mutant inhibitor into the blood or another bodily fluid). The amount of RECQL mutant inhibitor to be used is an amount effective to treat breast cancer in the subject, as defined above, and can be readily determined by the skilled artisan.

In the method of the present invention, where the RECQL mutant inhibitor is a protein, the RECQL mutant inhibitor can also be introduced to the subject by introducing into a sufficient number of cells of the subject a nucleic acid encoding the RECQL mutant inhibitor, in a manner permitting expression of the RECQL mutant inhibitor protein. The amount of nucleic acid encoding RECQL mutant inhibitor is an amount that will produce RECQL mutant inhibitor protein in an amount effective to treat breast cancer, as defined above, in the subject. This amount can be readily determined by the skilled artisan.

Nucleic acid encoding a RECQL mutant inhibitor, as well as any antisense oligonucleotide or other nucleotide inhibitor of RECQL or any nucleotide encoding regular RECQL, can be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, naked DNA transfer, and any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus.

It is also within the confines of the present invention that a nucleic acid encoding a RECQL inhibitor can be introduced into suitable cells in vitro, using conventional procedures, to achieve expression of the RECQL inhibitor in the cells. Cells expressing the RECQL inhibitor can then be introduced into a subject to treat breast cancer in vivo. In such an ex vivo gene therapy approach, the cells can be removed from the subject, subjected to DNA techniques to incorporate nucleic acid encoding the RECQL inhibitor, and then reintroduced into the subject.

Furthermore, it is within the confines of the present invention that the RECQL inhibitor of the present invention can be administered to a subject who has breast cancer, either alone or in combination with one or more antineoplastic drugs used to treat breast cancer. Examples of antineoplastic drugs with which the RECQL inhibitor can be combined include, without limitation, carboplatin, cyclophosphamide, doxorubicin, etoposide, and vincristine.

Additionally, it is within the confines of the present invention that a formulation of a RECQL inhibitor can be further associated with a pharmaceutically-acceptable carrier, thereby comprising a pharmaceutical composition. The pharmaceutically-acceptable carrier must be "acceptable" in the sense of being compatible with the other ingredients of the composition, and not deleterious to the recipient thereof. Examples of acceptable pharmaceutical carriers include, without limitation, carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition can be conveniently presented in unit dosage.

The formulations of the present invention can be prepared by methods well-known in the pharmaceutical art. For example, a RECQL inhibitor can be brought into association with a carrier or diluent, as a suspension or solution. Optionally, one or more accessory ingredients (e.g., buffers, flavoring agents, surface active agents or surfactants, and the like) also may be added. The choice of carrier will depend upon the route of administration. The pharmaceutical composition would be useful for administering the RECQL inhibitor of the present invention to a subject to treat breast cancer. The RECQL inhibitor is provided in an amount that is effective to treat breast cancer in the subject. That amount can be readily determined by the skilled artisan, as described above.

It is also within the confines of the present invention that a nucleic acid encoding normal RECQL can be introduced into suitable cells in vitro, using conventional procedures, to achieve expression of normal RECQL protein in the cells. Cells expressing RECQL can then be introduced into a subject to treat breast cancer in vivo. In such ex vivo gene therapy approaches, the cells can be removed from the subject, subjected to DNA techniques to incorporate nucleic acid encoding normal RECQL, and then reintroduced into the subject.

Agents that are reactive with the RECQL nucleic acid can decrease expression of the RECQL nucleic acid containing a mutation (e.g., by functioning as a transcription factor, an activator, or a repressor that binds to silencer sites and thereby prevents activator binding or transcription), and can be useful in the present invention.

Accordingly, the present invention further provides a method for treating breast cancer in a subject, by administering to the subject an amount of a RECQL modulator effective to treat the breast cancer in the subject. As defined above, "RECQL" includes a RECQL protein, a "RECQL analogue", and a "RECQL mutant". The subject, individual, or patient is preferably a human. In some embodiments, the subject is a mammal having helicases similar to RECQL.

The modulator of the present invention can be a protein, polypeptide, peptide, nucleic acid (including DNA or RNA), antibody, Fab fragment, F(ab')2 fragment, molecule, compound, antibiotic, drug, or other agent, as defined herein, that reduces RECQL mutant expression. Appropriate modulators of RECQL mutant expression can be identified by contacting a candidate agent with a cell transformed with a vector comprising the RECQL nucleic acid, and assessing the effect of the agent on expression of RECQL nucleic acid.

In the method of the present invention, a modulator of RECQL mutant expression is administered to a subject who has breast cancer in an amount effective to treat breast cancer in the subject, as defined above. The amount of a modulator of RECQL mutant expression effective to treat breast cancer in a subject in need of treatment will vary, depending on the particular factors of each case, including the type of breast cancer, the subject's weight, the severity of the subject's condition, and the method of administration. These amounts can be readily determined by the skilled artisan. The modulator of RECQL mutant expression can be administered to a subject by introducing the modulator into target cells of the subject, in accordance with any of the modes described herein for administering or introducing nucleic acids and proteins. The target cells include any of those described above.

In the method of the present invention, normal RECQL also can be administered to a subject by introducing into a sufficient number of cells of the subject a nucleic acid encoding normal RECQL, in a manner permitting expression of normal RECQL. The nucleic acid can be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus. The amount of nucleic acid encoding normal RECQL to be used is an amount that will express normal RECQL protein in an amount effective to treat breast cancer, as defined above. These amounts can be readily determined by the skilled artisan.

It is also within the confines of the present invention that a nucleic acid encoding normal RECQL can be introduced into suitable cells in vitro, using conventional procedures, to achieve expression in the cells of normal RECQL protein. Cells expressing normal RECQL can then be introduced into a subject to treat breast cancer in vivo. In such ex vivo gene therapy approaches, the cells can be removed from the subject, subjected to DNA techniques to incorporate nucleic acid encoding normal RECQL, and then reintroduced into the subject.

The present invention is described in the following Examples, which are set forth to aid in an understanding of the invention, and should not be construed to limit in any way the scope of the invention as defined in the claims which follow thereafter.

EXAMPLES

Example 1—Polish Study: Subjects

The inventor studied two non-overlapping groups of women with breast cancer. The first group included 144 women with familial breast cancer, who were subjects for the discovery phase of the study. The second group included 13,611 women with unselected breast cancer, who were subjects for the validation phase. The validation phase also included a control group of 4,702 cancer-free women. All patients and control subjects were white and ethnic Poles. The Polish study was approved by the ethics committee of Pomeranian Medical University, Szczecin, Poland. All study subjects provided a signed consent form for participating in the study.

Example 2—Polish Study: Discovery Phase

Cases 144 women with familial breast cancer, diagnosed in sixteen different centers in Poland between 2000 and 2012, were evaluated. All patients were diagnosed with invasive breast cancer. The diagnosis of cancer was confirmed through review of the pathology reports. Patients with purely intraductal or intralobular cancers were excluded (ductal carcinoma in situ or lobular carcinoma in situ). These patients were selected from a registry of familial breast cancer cases at the Hereditary Cancer Center in Szczecin on the basis that a high-quality DNA sample was available. Family history was collected at the time of interview. All cancer cases in first- and second-degree relatives and their ages of onset were recorded.

Whole exome sequencing was limited to 144 families, based on the costs of sequencing and the resources available to the research team. Families were prioritized for inclusion based on the number of breast cancer cases seen in the family and their ages of onset. In general, a family was eligible for testing if there were four cases of breast cancer (any ages), three cases of breast cancer (one under 50), or two cases of breast cancer (both under 50) on the same side of the family.

Among the 144 women with breast cancer, there were 34 women with three or more relatives affected, 82 women with two relatives affected, and 28 women with a single affected relative. Twelve of 144 (8.3%) women reported a family history of ovarian cancer. The mean age of breast cancer diagnosis among the 144 women was 48.0 years (age range, 29 to 65 years); 17 women (11.8%) were diagnosed below age 40, 83 women (57.6%) were diagnosed between ages 40 and 50, and 44 women (30.5%) were diagnosed above age 50. The mean age of onset of the probands who had a single affected relative was 45.6 years and the age of onset of their relatives was 47.8 years. All of the probands from the 144 families had tested negative for 11 Polish founder mutations in BRCA1 (p.Cys61Gly, c.4035delA, c.5263_5264insC, c.3700_3704delGTAAA, c.66_67delAG and p.Arg1751Ter), CHEK2 (c.444+1G>A, c.1100delC, del5395(exon10-11del), p.Ile157Thr) and NBS1 (c.657_661delACAAA).

Example 3—Polish Study: Validation Phase

Cases 13,611 prospectively ascertained unselected patients with invasive breast cancer, who were diagnosed from 1996 to 2013 at 18 different hospitals in Poland, were evaluated. The study was initiated in Szczecin in 1996, and was extended to Poznan in 1997 and Olsztyn in 1998. Fifteen other centers began recruiting patients in 2001. All patients diagnosed with invasive breast cancer at participating centers were eligible. Patients with purely intraductal or intralobular cancer were excluded (ductal carcinoma in situ or lobular carcinoma in situ), but patients with ductal carcinoma in situ with microinvasion were included. In seven centers, patients with breast cancer diagnosed at all ages were recruited (n=8860; age range, 18 to 92 years)=cohort 1. At eleven centers, only patients with early onset breast cancer, diagnosed at age 50 years or younger, were recruited (n=4751; age range, 22 to 50 years)=cohort 2. Patients were unselected for family history. The patient participation rate was 76.1%.

All 13,611 women tested negative for the presence of three common founder alleles in BRCA1 (p.Cys61Gly, c.4035delA, c.5263_5264insC), which account for 86% of all BRCA1/2 mutations seen in the Polish population. 576 women who carried one of these three BRCA1 Polish founder mutations were excluded.

In total, there were 13,611 BRCA1-mutation-negative women with breast cancer (age range, 18 to 92 years; mean, 53.2 years); 6,973 patients were diagnosed at age 50 years or younger, and 6,638 patients were diagnosed at age greater than 50 years.

A family history was taken either by the construction of a family tree or the completion of a questionnaire. All first- and second-degree relatives diagnosed with invasive breast cancer and their respective ages of diagnosis were recorded. The family history questionnaire was filled in by a patient or by a nurse. The detailed family tree was drawn by a physician. Family history data were collected for 11,508 of 13,611 (85%) women with breast cancer (including 32 carriers of c.1667_1667+3delAGTA mutation and 11,479 non-carriers). 1,840 of the 11,508 (16.0%) women (with family history data available) reported a first- or second-degree relative with breast cancer.

In addition, information was recorded on stage, grade, lymph node status, estrogen receptor status, multicentricity, and bilaterality for more than 70% of patients. Women with a previous contralateral breast cancer or with a current diagnosis of bilateral cancer were considered to be bilateral.

Controls

The control group included 4,702 cancer-free women, aged 18 to 94 years (mean age, 53.0 years). These controls were derived from 4 sources. The first subgroup consisted of 979 women from the region of Szczecin (age range, 24 to 84 years), who were chosen for this study to be age- and geographically-matched with a series of patients with incident breast cancer diagnosed in Szczecin between 1996 and 2004. These women were part of a population-based study of the 1.5 million residents of West Pomerania (North-West Poland), designed to identify familial aggregations of cancer, and were interviewed in 2007. The second control series consisted of 1,707 unselected women (age range, 32 to 72 years), who participated in ultrasonography (USG), mammography screening at 8 different centers all over Poland between 2009 and 2011 (Kielce, Kraków, Olsztyn, Poznań, Szczecin, Świdnica, Toruń, Zielona Góra) and provided blood samples for DNA analysis. Women with breast cancer and women with a positive family history of breast cancer were excluded from this group. The third control group included 1,031 unselected women (age range, 20 to 94 years), selected at random from the computerized patient lists of family practices located in the region of Opole (South Poland). These women, who were invited by mail to join the study, participated in 2012 and 2013. The fourth series included 985 Polish women (age range, 50 to 66 years), who participated in the population colonoscopy screening program for colorectal cancer between 2007 and 2010 in Szczecin, Bialystok, and Lódz and provided blood samples for DNA analysis.

The controls might not be perfectly matched with the cases, with respect to age and geographical region, but they are not also over-represented by a specific age group or city of origin. Almost half of the controls (38%, 1,788/4,702) were 50 years old or younger and the other half (62%, 2,914/4,702) were older than 50. The inventor found one RECQL c.1667_1667+3delAGTA mutation carrier in each of these two age groups. The geographical distribution of the cases and controls were about the same. The Polish cases and controls were derived from 18 and 15 Polish cities, respectively, from all over Poland. The distribution of the cases and controls was almost similar in the north (45% of cases and 57% of controls), center (15% of cases and 12% of controls), and south (40% of cases and 30% of controls) of Poland. The small differences seen here probably do not affect the overall result, since the inventor's study benefits from the homogeneity of the population. In fact, the RECQL c.1667_1667+3delAGTA mutation frequency was similar among cases from different regions (0.23% in the north, 0.19% in the center, and 0.26% in the south), of Poland and is expected to be the same among controls as well: Poland is populated by ethnic Slays, is genetically a homogenous country, and the frequency of other Polish founder mutations (BRCA1, CHEK2 and NBS1) is also similar in different regions of Poland. A detailed geographical distribution of cases and controls and the frequency of the RECQL c.1667_1667+3delAGTA mutation among them are shown in FIG. 7.

Example 4—French-Canadian Study: Subjects

The inventor studied two non-overlapping groups of women with breast cancer. The first group included 51 women with familial breast cancer used for the discovery phase of the study. The second group included 1,013 women with familial or young-age-at-onset breast cancer used for the validation phase. In the validation phase, the inventor also included a control group of 7,136 newborns. All patients and control subjects were white and French-Canadian. The French-Canadian study was approved by the ethics committee of McGill University, Montreal, Canada. All study subjects provided a signed consent form for participating in the study.

Example 5—French-Canadian Study: Discovery Phase

Fifty-one French-Canadian women with breast cancer were subjected to whole exome sequencing for the discovery phase of the study. They were recruited from hospitals in Montreal serving patients from different regions of the province of Quebec between 1995 and 2013. Their mean age of diagnosis was 43.8 years (age range, 23 to 62 years). Cases were selected on the basis of having a high likelihood of genetic predisposition in the form of a strong family history, bilateral disease, or early age of onset. Twelve women were diagnosed with their first cancer below 40 years of age, 36 between 40 and 50 years, and only 3 above 50 years old. Forty-five of these 51 women had 3 or more first- or second-degree relatives with breast cancer, 3 had 2 relatives, and 2 had a single affected relative. One patient did not have any first- or second-degree relatives with breast cancer, but she was diagnosed with invasive ductal carcinoma at age 23. All cases had received full sequencing and MLPA analysis to detect large insertions or deletions for BRCA1 and BRCA2 as well targeted mutation analysis to rule out the presence of a PALB2 founder mutation, Q775X, prior to inclusion in the study. Additionally, targeted mutation analyses previously performed in 12 of 51 subjects revealed no TP53 mutations as described previously [13, 42-44]. These 12 study subjects self-reported a grandparental French Canadian of Quebec, Canada and had a family history of breast cancer in at least two first-, second-, or third-degree relatives (to the breast-cancer-affected proband subjected to sequencing). DNA from peripheral blood leukocytes for each of these cases was provided by La Banque de tissus et de données of the RRCancer of the Fonds recherche Québec Santé (FRQS), which is affiliated with the Canadian Tumour Repository Network (CRTNet).

Example 6—French-Canadian Study: Validation Phase

Cases

Study subjects included 1,013 French-Canadian women, of whom 112 had ductal carcinoma in situ (DCIS) and 901 had invasive breast cancer (incident or prevalent), who were treated and followed at a single breast cancer clinic affiliated with the Research Center of University of Montreal (CR-CHUM). French-Canadian ancestry was self-defined or with reference to three or more French-Canadian grandparents. Women aged 51 to 70 years were eligible if they had two or more first- or second-degree relatives with breast or ovarian cancer. All women aged 50 or below were eligible, regardless of family history. Women were ineligible if the diagnosis occurred more than 10 years in the past.

Potential study subjects were identified through medical chart review and were approached to participate in the study. Participating subjects signed a consent form and completed a questionnaire containing information on known and suspected risk factors for breast-cancer as well as socio-demographic information. A blood sample was collected for genetic testing. A detailed family history was taken from each participating subject. For each patient, the pathology report was reviewed and the cancer was classified as invasive only, invasive with DCIS component, or DCIS alone. The estrogen receptor (ER) status was classified according to the pathology report (positive, negative, equivocal, missing). 1,075 eligible cases were tested who were either aged less than 50 years at diagnosis or who were 50 years or older and with at least two affected first- or second-degree relatives. Subjects were tested for seven founder mutations in BRCA1, BRCA2, and PALB2 (three in BRCA1, three in BRCA2, and one in PALB2) [14,39]; 1,013 eligible cases were negative for these seven mutations.

Controls

Newborn controls were collected at l'Hôpital Saint-François d'Assise maternity in Quebec City between 1996 and 2003. These samples were anonymized and unlinked. To assess allele frequency and rule out the possibility of common variants in the general French-Canadian population, the inventor initially genotyped in a total of 1,932 newborns from the Quebec City area for all RECQL mutations observed in French-Canadian cases. The inventor used the iPLEX® MassARRAY® platform (Sequenom, Inc., San Diego, Calif., USA) to genotype all four variants as part of a multiplex panel performed at McGill University and the Genome Québec Innovation Centre (Montreal, QC, Canada). The inventor then extended genotyping of the recurrent variant Arg215Ter to an additional 5,204 newborns using an allele-specific PCR assay. DNA samples were pooled in sets of 8 and further analyzed individually whenever presence of a variant was detected within a pooled set as described by Giroux et al. [40], with slight modifications. Two internal probes were designed to be specific to each allele (5'-3'-TCATCCACAGCAATTCG (SEQ ID NO:2) and 5'-3'-TCATCCACAGCAATTCA) (SEQ ID NO:3), while the common oligonucleotide used for each amplification was 5'-3'-GCTCTTCATTGGAGTATCTGTTTG (SEQ ID NO:4).

Example 7—Whole Exome Sequencing

Germline DNA was isolated from peripheral blood leukocytes using standard methods. The Agilent SureSelect™ human exome kit (V4) (Agilent Technologies, Inc., Santa Clara, Calif., USA) was used for library preparation, exome enrichment, and capturing sequence target regions. The kit captures 50 Mbp (1.7%) of the human genome, and covers coding exons in CCDS and RefSeq databases and exons annotated by the GENCODE project. This includes ~205,000 exons in ~35,000 genes, including protein coding and non-coding RNA genes.

The captured regions for each sample were barcoded, and every three samples were pooled and used for paired-end sequencing for 100 cycles (generating 100 bp reads) on a single lane of Illumina HiSeq™ 2000's flow-cell (Illumina, Inc., San Diego, Calif., USA) (performed at the McGill University and Genome Québec Innovation Centre, Montreal, QC, Canada).

The sequence reads for each exome sequence of each individual were aligned to the reference sequence of the human genome using Burrows-Wheeler Aligner [41]. The mean depth of coverage was 190× (range 92× to 225×). On average, 96.3% (range, 94.3% to 96.6%) of the CCDS exons were covered at 12× depth of coverage and higher was used for variant calling. The Picard package [45] was used to convert the SAM files to BAM format and to sort and index the BAM files. In the next step, all the unmapped reads, reads aligned to more than one human genome region, and all duplicate reads were filtered out from the BAM file using the GATK package [46]. Exact duplicate reads were collapsed to avoid inflated coverage. Indel realignment was performed with GATK IndelRealigner. The UnifiedGenotyper module of the GATK package was used for calling both SNPs and indels. Regions with at least 12-fold depth of coverage were used for calling variants and a different nucleotide from the reference sequence seen in at least 25% of the reads aligned to a given position was called as a variant. The SNP & Variation Suite (GoldenHelix Inc., Bozeman, Mont., USA) was used for annotating called variants. Annotation was used for determining the related genes and the effect of each variant on the coding proteins.

The inventor sought to identify variants that truncate the protein (insertions, deletions, and stop codon mutations) and variants at the consensus splice site which are likely to be dysfunctional. The inventor first focused on variants seen in two or more cases in each population, and then focused on genes with two or more singleton variants. The genes were then prioritized for a validation step based on the number of carriers seen in each population, whether seen in both populations, and whether their function was known to be important in cancer pathogenesis. The gene functions were curated manually.

Example 8—Sanger Sequencing

All deleterious RECQL variants identified by whole exome sequencing in the discovery phase were confirmed by Sanger direct sequencing. The entire coding regions of RECQL (NM_002907.3) were sequenced in 13 amplicons in the validation phase. Sanger sequencing was also used for genotyping the RECQL p.Arg215Ter mutation located in exon 6. Sequencing reactions were performed using a Big-Dye® Terminator v3.1 Cycle Sequencing Kit (Applied Biosystems/Life Technologies, Foster City, Calif., USA) according to the manufacturer's protocol.

Sequencing products were analyzed on the ABI PRISM® 3500XL Genetic Analyzer (Applied Biosystems/Life Technologies, Foster City, Calif., USA). All sequences were compared to the RECQL RefSeq sequence (NM_002907.3) for variant detection using Mutation Surveyor software (SoftGenetics LLC, State College, Pa., USA).

Example 9—Taqman Genotyping

DNA was isolated from 5 to 10 ml of peripheral blood. The RECQL c.1667_1667+3delAGTA mutation was genotyped using a TaqMan® assay (Applied Biosystems/Life Technologies, Foster City, Calif., USA) with primers (1665F: 5'-GACAACCTGA AAGAATAATG (SEQ ID NO:5) and 1665r: 5'-TGGAGAAGAT TATTGCACAC) (SEQ ID NO:6) and probes (1665del: 5'-GT TTG TAC ATA AGA TAC TGC T (SEQ ID NO: 7) and 1665 wt: 5'-GT TTG TAC ATA CTT AAG ATA CTG) (SEQ ID NO:8) using LightCycler® Real-Time PCR 480 System (Roche Life Science, Indianapolis, Ind., USA). Laboratory technicians were blinded to case-control status. The overall genotyping call rate was 99.3%. The presence of the mutation was confirmed by Sanger, as described above.

Example 10—mRNA Analysis

To analyze the effect of the RECQL c.1667_1667+3delAGTA mutation, the total RNA was extracted from white blood cells of four mutation carriers and three non-carriers and cDNA libraries were constructed. Total RNA was isolated from 3 ml of freshly collected venous blood using RNAzol® BD reagent (Molecular Research Center, Inc., Cincinnati, Ohio, USA), following the manufacturer's instructions, for all carriers of the c.1667_1667+3delAGTA mutation and some non-carriers. Isolated total RNA was immediately used for reverse transcription. cDNA was transcribed with Transcriptor First Strand cDNA Synthesis Kit (Roche Applied Science, Penzberg, Germany) using Oligo (dT) primers, following the manufacturer's instructions. An amplicon with 452 bp from RECQL mRNA was amplified using primers designed to overlap the region between exons 11-12 (forward primer) and exons 14-15 (reverse primer). The amplified RECQL mRNA was electrophoresed in a 3% agarose gel.

Both carriers of c.1667_1667+3delAGTA mutations (samples 4-7) and non-carriers (samples 1-3) showed the expected 452 bp DNA band, whereas only the mutation carriers (samples 4-7) showed a longer DNA fragment (I, sample 8 is a negative control). Sequencing of PCR products from non-carriers (A) and carriers (B) revealed that the extra fragment seen in carriers of the c.1667_1667+3delAGTA mutation does not have the deleted single nucleotide (A) at the 3' end of exon 13; however, it has an insertion of 28 bp from the 5' of intron 13 after three deleted nucleotides (GTA) of this intron. This mutation results in a net addition of 27 bp to the mRNA spliced from the mutated allele that results in the translation of loss of the lysine amino acid at codon 555 and an insertion of 10 amino acids (MYKLIHYSFR) (SEQ ID NO: 1) at codons 555 to 564 of the RECQL protein.

Figure 1B:
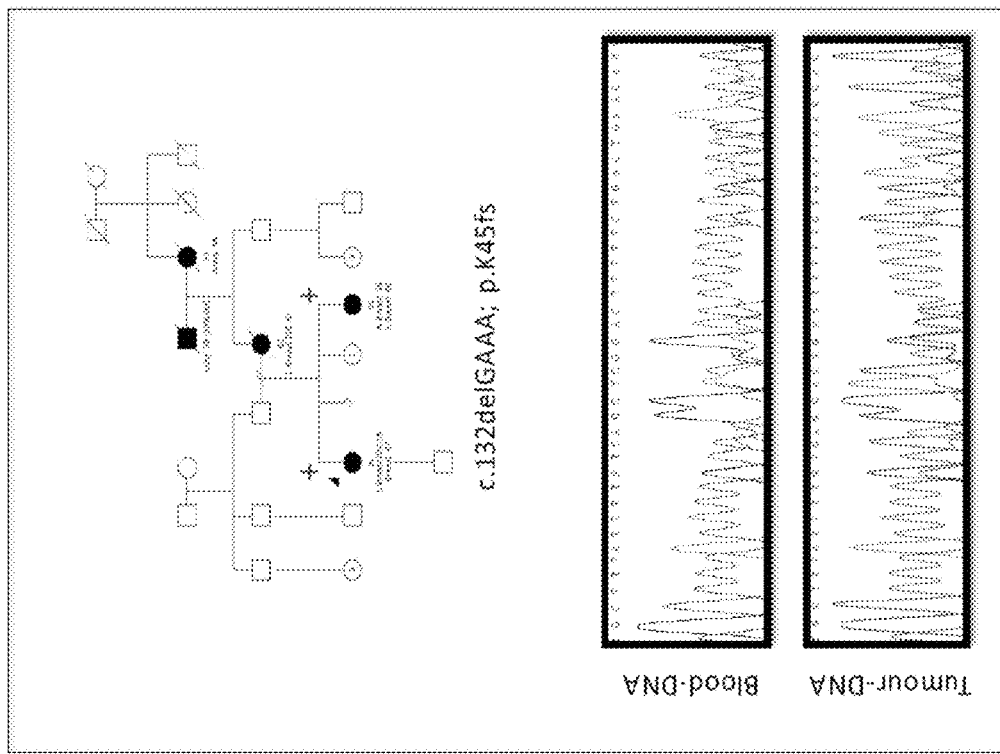

A fragment of RECQL cDNA was then amplified in a PCR reaction using primers which were designed to be located on exon junctions. Forward primer (5'-AAGCAAATGTCGTCGTGTGT 3') (SEQ ID NO:9) was designed to bind at the boundaries of exons 11 and 12 and the reverse primer (5'-CAGCCCTGAAAGAGTTCTGC 3') (SEQ ID NO:10) was designed to bind to the boundaries of exon 14 and 15. PCR products were visualized by gel-electrophoresis on a 3% agarose gel (FIGS. 1A and 1B). The PCR products corresponding to amplified fragments of RECQL cDNA were then sequenced from both 5' and 3' ends using the forward and reverse primers with BigDye® Terminator v3.1 Cycle Sequencing Kit (Applied Biosystems/Life Technologies, Foster City, Calif., USA), following the manufacturer's protocol. Sequencing products were analysed on the ABI PRISM® 3100 Genetic Analyzer (Applied Biosystems/Life Technologies, Foster City, Calif., USA) (FIGS. 1A and 1B).

Example 11—LOH Analysis

Unstained formalin-fixed, paraffin-embedded (FFPE) slides were dissected following pathology revision to select tumor and normal areas. DNA from breast and ovary FFPE tissue was isolated using the QIAGEN DNeasy® FFPE Tissue kit (Qiagen, Valencia, Calif., USA). 50 ngr of normal DNA and tumor DNA was amplified and Sanger sequenced in parallel. Conditions and procedures used to conduct the LOH analysis are known to a person skilled in the art.

Example 12—Data Analysis

All genotype comparisons between cases and controls were made using Fisher exact test, and two-tailed p-values were calculated. Odds ratios (OR) were calculated for each comparison plus their 95% confidence intervals.

Example 13—NHLBI Exome Data

The European-American population of the NHLBI exome sequencing database was used as an estimate for the RECQL mutation frequencies expected to be seen in the general population. The total number of truncating variants seen in the RECQL gene at the discovery phase were compared to the total number of truncating variants reported among the 4,300 European-American population of the NHLBI exome database; however, the inventor excluded two variants from the NHLBI exome variants. The first excluded variant was RECQL c.120-121insA, which seems to be a false positive mutation call at a homopolymer extension of nine adenine nucleotides; the inventor also saw this mutation in some of the discovery phase samples, but it was not confirmed by Sanger sequencing. The second excluded variant was RECQL p.Ser620Ter variant, which is located at the last exon of RECQL gene, just 50 codons before the gene original stop codon, and is expected to be non-deleterious to the RECQL protein function.

Results and Discussion

The results obtained from Examples 1-13 are summarized and discussed below.

To investigate breast cancer susceptibility genes, the inventor used whole exome sequencing (WES) to investigate familial BC patients selected from Polish and Quebec-based French-Canadian populations, two populations which harbour multiple founder mutations in other breast cancer susceptibility genes due to common ancestors [11-14]. The strategy in the initial discovery phase was to study a limited number of cancer families to identify genes for which multiple probands shared a common mutant allele. Then, through two validation phases, the inventor surveyed selected alleles of the candidate gene in much larger sets of breast cancer patients. In aggregate, the inventor studied 15,189 cases of BC and 11,838 controls. For the purposes of the study, the inventor included an over-representation of early-onset cases, but did not find an association with age of onset; the odds ratio may pertain to breast cancer at any age.

In the discovery phase, WES was conducted on 144 Polish and 51 French-Canadian women with BC. These cases were selected based on their strong BC family histories and/or their ages of onset. All were negative for the numerous founder mutations in BRCA1, BRCA2, CHEK2, NBN, and PALB2 that are present in the Polish and French-Canadian populations [11-14]. Some of the Polish cases, however, were found by WES [15] to carry non-founder mutations in several of these genes.

To prioritize genes for further study, the inventor identified those genes in which a truncating mutation (nonsense mutation, splicing site mutation, frame shift insertion or deletion, or start codon change mutation) was observed in at least two cases from each of the two populations. The inventor excluded from consideration those variants with a minor allele frequency greater than 1% (either in-house or in publicly-available mutation databases), assuming these to be benign or low penetrance variants. Several genes were identified in each population, but only one gene, RECQL, harbored multiple variants in both populations and had a function known to be related to cancer.

Among the 195 Polish and French-Canadian cases studied in the discovery phase, the inventor identified five patients (2.6%) who carried different truncating mutations in RECQL (FIG. 4) confirmed by Sanger sequencing. In comparison, eight RECQL truncating mutation carriers were seen among 4,300 European-American individuals (0.2%) in the NHLBI database [16] (p=0.0002). Although the NHLBI samples are not from Polish or French-Canadian individuals, the marked difference in the prevalence of truncating mutations seen in the NHLBI database, compared with the breast cancer cases studied by the inventor, was sufficiently large to warrant the further investigation of RECQL. Two mutation carriers also had a positive family history of ovarian cancer. In two French-Canadian pedigrees (c.132_135delGAAA, c.426delT), one affected relative was tested by Sanger sequencing to confirm carrier status (FIGS. 1A and 1B). DNA was also available from the BCs of the probands in these two pedigrees; Sanger sequencing of RECQL in the tumour tissues did not show loss of heterozygosity or a second hit mutation in RECQL. Finally, the inventor observed four missense variants among these 195 patients, all with MAF ≤1% among the European-American population of the NHLBI study (FIG. 5); all were confirmed by Sanger sequencing.

In the first validation phase, the inventor sequenced the entire 14 coding exons of RECQL (NM_002907.3) among a non-overlapping set of 950 familial BC cases (475 Polish, 475 French-Canadian) who were negative for BRCA1 and BRCA2 population-specific founder mutations. Although none of the original five RECQL mutations identified in the discovery phase was observed, two other truncating mutations were identified among the 950 cases (FIG. 4). One mutation (c.1667_1667+3delAGTA) was seen in two Polish BC patients, and the other mutation (c.643C>T, p.Arg215Ter) was seen in two French-Canadian patients. The inventor also identified a total of 12 missense variants in RECQL among 19 of the 950 BC patients who all had a MAF ≤1% among the European-American population of the NHLBI study (FIG. 5). Two of the four missense mutations (p.Cys129Tyr, p.Thr134Ile) were predicted to be pathogenic by Combined Annotation Dependent Depletion (CADD) algorithm [47]. No missense mutation was found in RECQL gene among the 54 French-Canadian patients.

The recurrent mutations seen twice among BC patients and families of each founder population (FIG. 4) were considered more likely to represent founder mutations than were the original WES-identified mutations (seen only one time each). These recurrent mutations were selected for genotyping in additional BC cases and population control cohorts representing each founder population for the second validation phase. The Polish c.1667_1667+3delAGTA mutation in RECQL was genotyped in 13,136 unselected BC patients and 4,702 adult Polish cancer-free female controls. This mutation was found in 30 cases (0.23%) and in two controls (0.04%; odds ratio (OR)=5.4; 95% CI: 1.3-46; p=0.008). The p.Arg215Ter mutation was genotyped in 538 French-Canadian BC cases and 7,136 newborn French-Canadian controls. The French-Canadian cases were early-onset cases (aged less than 50 years at diagnosis) or had at least two affected first- or second-degree relatives. The p.Arg215Ter mutation was seen in five more cases and in one control. Therefore, the frequency of this stop-codon mutation among the two higher-risk sets of French-Canadian patients studied in the validation phase was 0.69% (7/1,013) compared to 0.014% (1/7,136) in controls (p=0.000003).

Figure 2:
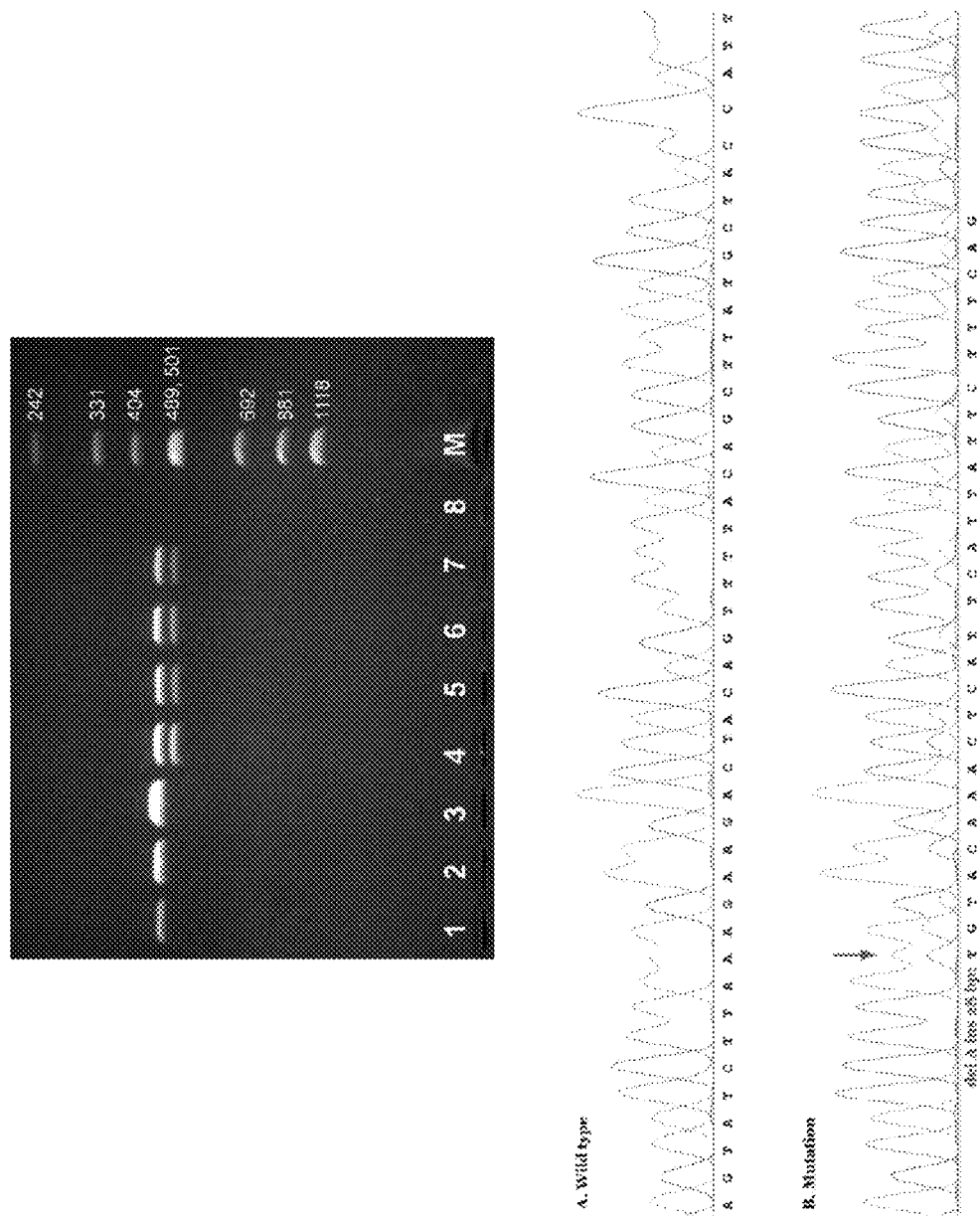
FIG. 2 shows the effect of the RECQL c.1667_1667+3delAGTA mutation on the expression of RECQL mRNA.

Sequencing of RECQL mRNA from carriers of the c.1667_1667+3delAGTA mutation showed an insertion of 28 bp from the 5' end of intron 13 following a three-nucleotides deletion (GTA) of this intron. Therefore, this mutation results in a net addition of 27 bp to the mRNA spliced from the mutated allele that translates in the deletion of lysine at codon 555 and a subsequent insertion of 10 amino acids (MYKLIHYSFR, codons 555 to 564) (FIG. 2). This in-frame indel displaces residues 558-566, which form a β-hairpin in the secondary structure of the RECQL protein that is essential for unwinding the replication fork; this structural pin with its tyrosine residue (Tyr564) at the tip seems to function as a DNA strand separator [17].

Figure 3:
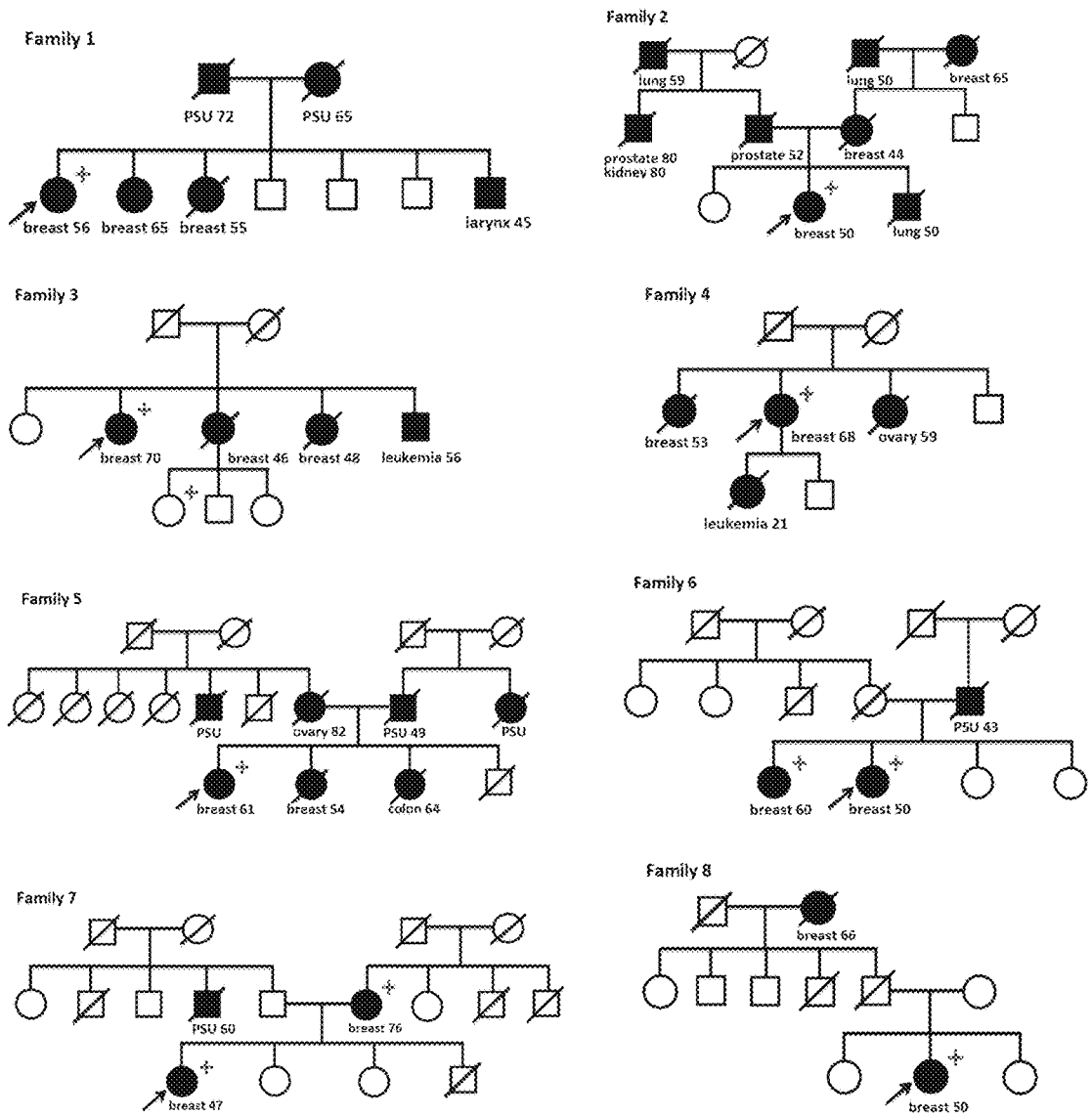
FIG. 3 shows the pedigrees of nine RECQL c.1667_1667+3delAGTA mutation carriers, each with a positive family history of breast cancer, who were identified from 13,611 women with breast cancer not selected for a family history of cancer. The type of cancer and age of diagnosis are indicated next to the symbol. (+)=mutation carriers; PSU="primary cancer site unknown".

The mean age at BC diagnosis was 54.5 years among all 32 Polish carriers of the RECQL c.1667_1667+3delAGTA mutation found in the inventor's investigation, which was not different from the age at diagnosis among all non-carriers (53.2 years, p=0.5). Nine of 31 Polish mutation carriers with family information had a family history of BC (FIG. 3) among their first- and/or second-degree relatives (29%), compared to 1,831 of 11,477 non-carrier cases with available family history information (15.9%) (OR=2.2; 95% CI: 0.99 to 4.7; p-value=0.09). Co-segregation of the mutation and breast cancer was shown for all three families with available DNA from relatives (FIGS. 1A and 1B). There was no difference between the clinical characteristics of the RECQL mutation carriers and non-carriers (FIG. 6). There was also no significant difference between the age at diagnosis of all seven French-Canadian carriers of the RECQL p.Arg215Ter mutation (48.9 years) and non-carriers (47.6 years, p=0.7).

RECQL, also known as RECQL1 or RECQ1, is on chromosome 12p12. It encodes a DNA helicase protein with 649 residues that belongs to a class of DExH-containing DNA helicases [18, 19]. The RECQL protein has a helicase domain which is responsible for the helicase catalytic function of the protein and also a RecQ C-terminal (RQC) domain which is involved in the protein's binding to DNA and other proteins [20]. The RECQ helicases that unwind dsDNA are involved in several important cellular functions, including DNA repair, replication, recombination, and transcription [20]. There are five known RECQ genes, of which three (BLM, WRN, and RECQL4) have been identified in association with distinct genetic disorders that share the common feature of an elevated risk for developing various cancers [21-23].

For instance, mutations in the BLM gene results in Bloom syndrome, characterized by dwarfism, sunlight sensitivity, skin disorders, immunodeficiency, male sterility, chromosome breakage, and a high risk of developing both leukemia and solid tumours [21]. A founder allele of the BLM gene, c.1642C>T (p.Gln548Ter), has also been identified in Slavic populations of Eastern Europe (48, 49) that increases the risk of breast cancer (OR=5.7; 95% CI: 2.0 to 15.9; p=3.7×10$^4$). WRN gene mutations cause Werner syndrome, which is characterized by chromosome instability (including translocations and deletions), premature aging, osteoporosis, diabetes, and a high risk for a range of cancers [22]. Rothmund-Thomson syndrome is caused by mutations in the RECQL4 gene. This chromosome instability syndrome is characterized by premature aging, growth deficiency, and a higher risk for cancers, especially osteogenic sarcomas [23]. RECQ4 mutations have been also reported in association with skeletal anomalies [50, 51]. Prior to this study, no human disorder had been associated with mutations in the other two genes, RECQL and RECQL5.

Phenotypes seen in RECQL-depleted mouse and human cells suggest that RECQL has an important function in the regulation of genome integrity. Primary embryonic fibroblasts from Recql knocked down mice showed aneuploidy, spontaneous and frequent chromosomal breakage, and translocations [24]. Both mice and human RECQL-depleted cells displayed a high rate of spontaneous sister chromatid exchange (SCE), were more sensitive to ionizing radiation, and showed high load dsDNA breaks as measured by an increased number of γH2AX foci [24-26]. These all suggest that RECQL plays a role in homologous recombination (HR) repair of dsDNA breaks or prevents dsDNA breaks from happening in the first place [25]. Recent evidence is more in favor of the latter scenario. RECQL prevents dsDNA breaks by stabilising stalled or regressed replication forks [27]. Restabilising of the stalled replication fork [27] could potentially result in dsDNA break if it is not resolved in a timely manner.

RECQL-depleted cells also display reduced cell growth [25], indicating an important role in DNA replication. This is consistent with the observation of hypersensitivity of RECQL-depleted cells to topoisomerase I (TOP1) inhibitors such as camptothecins [25]. TOP1 facilitates DNA replication by resolving positive DNA supercoils (overwound DNA) produced by routine DNA processes such as gene transcription. TOP1 inhibitors are a class of chemotherapeutic drugs which intervene in cancer cell proliferation by perturbing this procedure, resulting in accumulation of positive DNA supercoils ahead of the replication machinery that stops the progress of the replication fork [31]. It is suggested that RECQL in conjunction with Poly ADP ribose polymerase could restart the stalled replication fork after cells are treated with TOP1 inhibitors [27] and that is why RECQL-depleted cells are more sensitive to TOP1 inhibitors.

Finally, RECQL has been shown to be involved in non-homologous end joining DNA repair [28] and lengthening of telomeres without telomerase [29]. These observations suggest a tumour suppressor role for RECQL, which is consistent with the fact that loss of heterozygosity of chromosome 12p12 has been frequently seen in solid tumours such as non-small-cell lung cancer [30] and in hematological malignancies like acute lymphoblastic leukemia (32). However, the expression level of RECQL protein is elevated in most cancers studied, including head and neck squamous cell carcinoma [33] and hepatocellular carcinoma [34], and in cell lines from ovarian, prostate, lung, liver, and pancreatic carcinomas [26]. It was also shown that proliferation of these cancer cells was inhibited through induction of mitotic catastrophe and mitotic cell death by silencing RECQL using small interference RNA; in contrast, normal growing RECQL-depleted fibroblasts did not show mitotic cell death [26]. Of the 455 breast cancer tumour samples with available expression data in the Catalogue of Somatic Mutations in Cancer (COSMIC) database, 8.7% and 1.5% showed high and low expression of RECQL gene, respectively [35].

The tumour suppressor function of RECQL and its involvement in predisposition to breast cancer may seem to be paradoxical in view of the high expression of the gene seen in cancer cells. However, it is important to consider the role that RECQL plays in DNA replication and how highlyproliferative cells, like cancer cells, would probably need it to survive. It is suggested that normal cells require fully-intact RECQL function to ensure their genome integrity. When the cells lose one or both copies of the gene, they are still viable, but are prone to cancer because of the genomic instability resulting from defective RECQL function. After transformation into tumor cells, though, these cells will be highly dependent on RECQL function to survive.

Proliferative tumor cells are more dependent on the RECQL protein because, like most cancer cells, they lack a proper G2 checkpoint system. RECQL can help cells avoid accumulation of DNA damage in S and G2 phases of the cell cycle that could carry over to M phase [26]. On the other hand, normal cells with a functioning G2 checkpoint provide enough time for repairing DNA damage resulting from defective RECQL function before progressing to M phase, which is why RECQL-depleted normal cells do not show mitotic catastrophe and cell death [26]. Cancer cells may also be more dependent on the RECQL protein because these cells use an Alternative Lengthening of Telomeres (ALT) mechanism for maintaining telomeres in parallel with routinely-used telomerase function in normal cells [36, 37], and RECQL is a key partner of the ALT pathway [29]. Therefore, the high expression of RECQL in cancer cells is secondary to acquiring a tumor phenotype in these cells; otherwise, RECQL is a tumour suppressor in normal cells by maintaining integrity of the cell's genome.

Based on the dependence of cancer cells on RECQL function and a distinctive sensitivity of tumour cells (compared with normal cells) to inhibition of RECQL activity, RECQL has been suggested as a therapeutic target for cancer [26, 33, 34]. Mitotic cell death in cancer cells, by inhibition of RECQL activity, happens in the short term, while tumorigenicity in normal cells is probably due to a long-term misfunctioning of the RECQL protein. In addition, since the RECQL protein restarts reversed replication forks after cells are treated with TOP1 inhibitors, it is suggested that down-regulation of RECQL in combination with TOP1 inhibitors could improve efficacy in treating cancer patients [27]. Similarly, the inventor expects that breast cancer patients who are carriers of deleterious RECQL mutations might also respond better to TOP1 inhibitors, such as Camptosar and Hycamtin.

One of the founder mutations associated with increased risk of breast cancer in the inventor's study was p.Arg215Ter (found in the French-Canadian population). p.Arg215Ter is a truncating mutation: the translated protein will not have any of the two RECQL protein's functional domains of helicase and RQC, although the RECQL mRNA copies carrying this truncating mutation are expected to be removed by the nonsense-mediated mRNA decay (NMD) pathway. The other RECQL founder mutation identified in the inventor's study was c.1667_1667+3delAGTA (seen in the Polish population). The inventor's expression analysis showed that this mutation results in inclusion of part of intron 13 (28 bp from its 5' end after the three deleted nucleotides) into the RECQL mRNA. The net effect of this four-nucleotide deletion and then insertion of 28 intronic base pairs is deletion of lysine amino acid at codon 555 and insertion of 10 amino acids at codons 555-564 (p.Lys555delinsMetTyr LysLeuIleHisTyrSerPheArg) on the translated RECQL protein. This in-frame indel displaces residues 558-566 which form a β-hairpin in the secondary structure of the RECQL protein [17]. The β-hairpin is essential for unwinding the replication fork; this structural pin, with its Tyrosine residue (Tyr564) at the tip, seems to function as a DNA strand separator [17] and p.Tyr564Ala RECQL mutant protein does not have DNA unwinding activity [17]. The β-hairpin structure is also important in binding of RECQL proteins to each other and forming protein oligomers, which are necessary for DNA strand annealing activity and for resolving HJ DNA structures [38]. It was shown that residues 560-562 of the β-hairpin are specifically important for making protein dimers by forming interstrand hydrogen bands, and mutated alleles at each of the three codons (Ser560, Phe561, and Thr562) were incapable of forming a RECQL protein dimer [38]. The deletion of lysine at codon 555 and insertion of 10 amino acids at codon 555-564 resulting from the c.1667_1667+3delAGTA mutation could potentially disrupt this β-hairpin structure in RECQL protein and make it dysfunctional.

REFERENCES

1. Couch F J, Nathanson K L, Offit K. Two decades after BRCA: setting paradigms in personalized cancer care and prevention. *Science,* 2014 Mar. 28, 343(6178):1466-70.
2. Miki Y, Swensen J, Shattuck-Eidens D, Futreal P A, Harshman K, Tavtigian S, Liu Q, Cochran C, Bennett L M, Ding W, et al. A strong candidate for the breast and ovarian cancer susceptibility gene BRCA1. *Science,* 1994 Oct. 7, 266(5182):66-71.
3. Wooster R, Bignell G, Lancaster J, Swift S, Seal S, Mangion J, Collins N, Gregory S, Gumbs C, Micklem G. Identification of the breast cancer susceptibility gene BRCA2. *Nature,* 1995 Dec. 21-28, 378(6559):789-92.
4. Rahman N, Seal S, Thompson D, Kelly P, Renwick A, Elliott A, Reid S, Spanova K, Barfoot R, Chagtai T, Jayatilake H, McGuffog L, Hanks S, Evans D G, Eccles D; Breast Cancer Susceptibility Collaboration (U K), Easton D F, Stratton M R. PALB2, which encodes a BRCA2-interacting protein, is a breast cancer susceptibility gene. *Nat Genet.,* 2007 February, 39(2): 165-7.
5. Bogdanova N, Feshchenko S, Schürmann P, Waltes R, Wieland B, Hillemanns P, Rogov Y I, Dammann O, Bremer M, Karstens J H, Sohn C, Varon R, Dörk T. Nijmegen Breakage Syndrome mutations and risk of breast cancer. *Int J Cancer,* 2008 Feb. 15, 122(4):802-6.
6. Meijers-Heijboer H, van den Ouweland A, Klijn J, Wasielewski M, de Snoo A, Oldenburg R, Hollestelle A, Houben M, Crepin E, van Veghel-Plandsoen M, Elstrodt F, van Duijn C, Bartels C, Meijers C, Schutte M, McGuffog L, Thompson D, Easton D, Sodha N, Seal S, Barfoot R, Mangion J, Chang-Claude J, Eccles D, Eeles R, Evans D G, Houlston R, Murday V, Narod S, Peretz T, Peto J, Phelan C, Zhang H X, Szabo C, Devilee P, Goldgar D, Futreal P A, Nathanson K L, Weber B, Rahman N, Stratton M R; CHEK2-Breast Cancer Consortium. Low-penetrance susceptibility to breast cancer due to CHEK2 (*)1100delC in noncarriers of BRCA1 or BRCA2 mutations. *Nat Genet.,* 2002 May, 31(1):55-9.
7. Renwick A, Thompson D, Seal S, Kelly P, Chagtai T, Ahmed M, North B, Jayatilake H, Barfoot R, Spanova K, McGuffog L, Evans D G, Eccles D; Breast Cancer Susceptibility Collaboration (U K), Easton D F, Stratton M R, Rahman N. ATM mutations that cause ataxia-telangiectasia are breast cancer susceptibility alleles. *Nat Genet.,* 2006 August, 38(8):873-5.
8. Li J, Yen C, Liaw D, Podsypanina K, Bose S, Wang S I, Puc J, Miliaresis C, Rodgers L, McCombie R, Bigner S H, Giovanella B C, Ittmann M, Tycko B, Hibshoosh H, Wigler M H, Parsons R. PTEN, a putative protein tyrosine phosphatase gene mutated in human brain, breast, and prostate cancer. *Science,* 1997 Mar. 28, 275(5308):1943-7.
9. Malkin D, Li F P, Strong L C, Fraumeni J F Jr, Nelson C E, Kim D H, Kassel J, Gryka M A, Bischoff F Z, Tainsky M A, et al. Germ line p53 mutations in a familial syndrome of breast cancer, sarcomas, and other neoplasms. *Science,* 1990 Nov. 30, 250(4985):1233-8.
10. Górski B, Byrski T, Huzarski T, Jakubowska A, Menkiszak J, Gronwald J, Pluzafiska A, Bebenek M, Fischer-Maliszewska L, Grzybowska E, Narod S A, Lubiliski J. Founder mutations in the BRCA1 gene in Polish families with breast-ovarian cancer. *Am J Hum Genet.,* 2000 June, 66(6):1963-8.
11. Cybulski C, Wokolorczyk D, Huzarski T, Byrski T, Gronwald J, Górski B, Debniak T, Masojć B, Jakubowska A, van de Wetering T, Narod S A, Lubiliski J. A deletion in CHEK2 of 5,395 bp predisposes to breast cancer in Poland. *Breast Cancer Res Treat.,* 2007 March, 102(1):119-22.
12. Steffen J, Nowakowska D, Niwińska A, Czapczak D, Kluska A, Piatkowska M, Wiśniewska A, Paszko Z. Germline mutations 657del5 of the NBS1 gene contribute significantly to the incidence of breast cancer in Central Poland. *Int J Cancer,* 2006 Jul. 15, 119(2):472-5.
13. Tonin P N, Mes-Masson A M, Futreal P A, Morgan K, Mahon M, Foulkes W D, Cole D E, Provencher D, Ghadirian P, Narod S A. Founder BRCA1 and BRCA2 mutations in French Canadian breast and ovarian cancer families. *Am J Hum Genet.,* 1998 November, 63(5):1341-51.
14. Foulkes W D, Ghadirian P, Akbari M R, Hamel N, Giroux S, Sabbaghian N, Darnel A, Royer R, Poll A, Fafard E, Robidoux A, Martin G, Bismar T A, Tischkowitz M, Rousseau F, Narod S A. Identification of a novel truncating PALB2 mutation and analysis of its contribution to early-onset breast cancer in French-Canadian women. *Breast Cancer Res.,* 2007, 9(6):R83.
15. Cybulski C, Lubinski J, Wokolorczyk D, Kuźniak W, Kashyap A, Sopik V, Huzarski T, Gronwald J, Byrski T, Szwiec M, Jakubowska A, Gorski B, Debniak T, Narod S A, Akbari M R. Mutations predisposing to breast cancer in 12 candidate genes in breast cancer patients from Poland. *Clin Genet,* 2014 Oct. 20 [Epub ahead of print].
16. Exome Variant Server, NHLBI GO Exome Sequencing Project (ESP), Seattle, Wash. (URL: http://evs.gs.washington.edu/EVS/) [July 2014]
17. Pike A C, Shrestha B, Popuri V, Burgess-Brown N, Muzzolini L, Costantini S, Vindigni A, Gileadi O. Structure of the human RECQ1 helicase reveals a putative strand-separation pin. *Proc Natl Acad Sci USA,* 2009 Jan. 27, 106(4):1039-44.
18. Puranam K L, Blackshear P J. Cloning and characterization of RECQL, a potential human homologue of the *Escherichia coli* DNA helicase RecQ. *J Biol Chem,* 1994 Nov. 25, 269(47):29838-45.
19. Seki M, Miyazawa H, Tada S, Yanagisawa J, Yamaoka T, Hoshino S, Ozawa K, Eki T, Nogami M, Okumura K, et al. Molecular cloning of cDNA encoding human DNA helicase Q1 which has homology to *Escherichia coli* Rec Q helicase and localization of the gene at chromosome 12p12. *Nucleic Acids Res,* 1994 Nov. 11, 22(22):4566-73.
20. Sharma S, Doherty K M, Brosh R M Jr. Mechanisms of RecQ helicases in pathways of DNA metabolism and maintenance of genomic stability. *Biochem J.,* 2006 Sep. 15, 398(3):319-37.
21. Ellis N A, Groden J, Ye T Z, Straughen J, Lennon D J, Ciocci S, Proytcheva M, German J. The Bloom's syndrome gene product is homologous to RecQ helicases. *Cell,* 1995 Nov. 17, 83(4):655-66.
22. Yu C E, Oshima J, Fu Y H, Wijsman E M, Hisama F, Alisch R, Matthews S, Nakura J, Miki T, Ouais S, Martin G M, Mulligan J, Schellenberg G D. Positional cloning of the Werner's syndrome gene. *Science,* 1996 Apr. 12, 272(5259):258-62.
23. Kitao S, Shimamoto A, Goto M, Miller R W, Smithson W A, Lindor N M, Furuichi Y. Mutations in RECQL4 cause a subset of cases of Rothmund-Thomson syndrome. *Nat Genet.,* 1999 May, 22(1):82-4.
24. Sharma S, Stumpo D J, Balajee A S, Bock C B, Lansdorp P M, Brosh R M Jr, Blackshear P J. RECQL, a member of the RecQ family of DNA helicases, suppresses chromosomal instability. *Mol Cell Biol.,* 2007 March, 27(5):1784-94.
25. Sharma S, Brosh R M Jr. Human RECQ1 is a DNA damage responsive protein required for genotoxic stress resistance and suppression of sister chromatid exchanges. *PLoS One,* 2007 Dec. 12, 2(12):e1297.
26. Futami K, Kumagai E, Makino H, Goto H, Takagi M, Shimamoto A, Furuichi Y. Induction of mitotic cell death in cancer cells by small interference RNA suppressing the expression of RecQL1 helicase. Cancer Sci., 2008 January, 99(1):71-80.
27. Berti M, Ray Chaudhuri A, Thangavel S, Gomathinayagam S, Kenig S, Vujanovic M, Odreman F, Glatter T, Graziano S, Mendoza-Maldonado R, Marino F, Lucic B, Biasin V, Gstaiger M, Aebersold R, Sidorova J M, Monnat R J Jr, Lopes M, Vindigni A. Human RECQ1 promotes restart of replication forks reversed by DNA topoisomerase I inhibition. *Nat Struct Mol Biol.,* 2013 March, 20(3):347-54.
28. Parvathaneni S, Stortchevoi A, Sommers J A, Brosh R M Jr, Sharma S. Human RECQ1 interacts with Ku70/80 and modulates DNA end-joining of double-strand breaks. *PLoS One,* 2013 May 1, 8(5):e62481.
29. Popuri V, Hsu J, Khadka P, Horvath K, Liu Y, Croteau D L, Bohr V A. Human RECQL1 participates in telomere maintenance. *Nucleic Acids Res.,* 2014, 42(9):5671-88.
30. Grepmeier U, Dietmaier W, Merk J, Wild P J, Obermann E C, Pfeifer M, Hofstaedter F, Hartmann A, Woenckhaus M. Deletions at chromosome 2q and 12p are early and frequent molecular alterations in bronchial epithelium and NSCLC of long-term smokers. *Int J Oncol.,* 2005 August, 27(2):481-8.
31. Koster D A, Palle K, Bot E S, Bjornsti M A, Dekker N H. Antitumour drugs impede DNA uncoiling by topoisomerase I. *Nature,* 2007 Jul. 2, 448(7150):213-7.
32. Montpetit A, Larose J, Boily G, Langlois S, Trudel N, Sinnett D. Mutational and expression analysis of the chromosome 12p candidate tumor suppressor genes in pre-B acute lymphoblastic leukemia. *Leukemia,* 2004 September, 18(9):1499-504.
33. Arai A, Chano T, Futami K, Furuichi Y, Ikebuchi K, Inui T, Tameno H, Ochi Y, Shimada T, Hisa Y, Okabe H. RECQL1 and WRN proteins are potential therapeutic targets in head and neck squamous cell carcinoma. *Cancer Res.,* 2011 Jul. 1, 71(13):4598-607.
34. Futami K, Ogasawara S, Goto H, Yano H, Furuichi Y. RecQL1 DNA repair helicase: A potential tumor marker and therapeutic target against hepatocellular carcinoma. *Int J Mot Med.,* 2010 April, 25(4):537-45.
35. Bamford S, Dawson E, Forbes S, Clements J, Pettett R, Dogan A, Flanagan A, Teague J, Futreal P A, Stratton M R, Wooster R. The COSMIC (Catalogue of Somatic Mutations in Cancer) database and website. *Br J Cancer,* 2004 Jul. 19, 91(2):355-8.
36. Henson J D, Neumann A A, Yeager T R, Reddel R R. Alternative lengthening of telomeres in mammalian cells. *Oncogene,* 2002 Jan. 21, 21(4):598-610.
37. Cho N W, Dilley R L, Lampson M A, Greenberg R A. interchromosomal homology searches drive directional ALT telomere movement and synapsis. *Cell,* 2014 Sep. 25, 159(1):108-21.
38. Lucic B, Zhang Y, King O, Mendoza-Maldonado R, Berti M, Niesen F H, Burgess-Brown N A, Pike A C, Cooper C D, Gileadi O, Vindigni A. A prominent β-hairpin structure in the winged-helix domain of RECQ1 is required for DNA unwinding and oligomer formation. *Nucleic Acids Res.,* 2011 March, 39(5):1703-17.
39. Ghadirian P, Robidoux A, Nassif E, Martin G, Potvin C, Patocskai E, Younan R, Larouche N, Venne A, Zhang S, Royer R, Narod S A. Screening for BRCA1 and BRCA2 mutations among French-Canadian breast cancer cases attending an outpatient clinic in Montreal. *Clin Genet,* 2014 January, 85(1):31-5.
40. Giroux S, Dubé-Linteau A, Cardinal G, Labelle Y, Laflamme N, Giguère Y, Rousseau F. Assessment of the prevalence of the 985A>G MCAD mutation in the French-Canadian population using allele-specific *PCR. Clin. Genet,* 2007 June, 71(6):569-75.
41. Li H and Durbin R. Fast and accurate short read alignment with Burrows-Wheeler transform. *Bioinformatics,* 2009, 25:1754-60.
42. Cavallone L, Arcand S L, Maugard C M et al. Comprehensive BRCA1 and BRCA2 mutation analyses and review of French Canadian families with at least three cases of breast cancer. *Fam. Cancer,* 2010, 9: 507-517.
43. Arcand S L, Maugard C M, Ghadirian P et al. Germline TP53 mutations in BRCA1 and BRCA2 mutation-negative French Canadian breast cancer families. *Breast Cancer Res. Treat.,* 2008, 108(3):399-408.
44. Tischkowitz M, Sabbaghian N, Hamel N et al. Contribution of the PALB2 c.2323C>T [p.Q775X] founder mutation in well-defined breast and/or ovarian cancer families and unselected ovarian cancer cases of French Canadian descent. *BMC Med. Genet.,* 2013, 14: 5.
45. Picard. http://picard.sourceforge.net.
46. McKenna A, Hanna M, Banks E, et al. The Genome Analysis Toolkit: a MapReduce framework for analyzing next-generation DNA sequencing data. *Genome Res.,* 2010, 20:1297-303.
47. Ng S B, Buckingham K J, Lee C, et al. Exome sequencing identifies the cause of a mendelian disorder. *Nat. Genet.,* 2010, 42(1):30-5.
48. Prokofyeva D, Bogdanova N, Dubrowinskaj a N, Bermisheva M, Takhirova Z, Antonenkova N, Turmanov N, Datsyuk I, Gantsev S, Christiansen H, Park-Simon T W, Hillemanns P, Khusnutdinova E, Dork T. Nonsense mutation p.Q548X in BLM, the gene mutated in Bloom's syndrome, is associated with breast cancer in Slavic populations. *Breast Cancer Res. Treat.,* 2013 January, 137(2):533-9.
49. Sokolenko A P, Iyevleva A G, Preobrazhenskaya E V, Mitiushkina N V, Abysheva S N, Suspitsin E N, Kuligina E Sh, Gorodnova T V, Pfeifer W, Togo A V, Turkevich E A, Ivantsov A O, Voskresenskiy D V, Dolmatov G D, Bit-Sava E M, Matsko D E, Semiglazov V F, Fichtner I, Larionov A A, Kuznetsov S G, Antoniou A C, Imyanitov E N. High prevalence and breast cancer predisposing role of the BLM c.1642 C>T (Q548X) mutation in Russia. *Int. J. Cancer,* 2012 Jun. 15, 130(12):2867-73.
50. Siitonen H A, Kopra O, Kääriäinen H, Haravuori H, Winter R M, Säämänen A M, Peltonen L, Kestilä M. Molecular defect of RAPADILINO syndrome expands the phenotype spectrum of RECQL diseases. *Hum. Mol. Genet.,* 2003 Nov. 1, 12(21):2837-44.
51. Van Maldergem L, Siitonen H A, Jalkh N, Chouery E, De Roy M, Delague V, Muenke M, Jabs E W, Cai J, Wang L L, Plon S E, Fourneau C, Kestilä M, Gillerot Y, Megarbané A, Verloes A. Revisiting the craniosynostosis-radial ray hypoplasia association: Baller-Gerold syndrome caused by mutations in the RECQL4 gene. *J. Med. Genet.,* 2006 February, 43(2):148-52.

All publications mentioned herein are hereby incorporated by reference in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for treating breast cancer in a subject, comprising analyzing a diagnostic sample of the subject for the presence of at least one mutation in the RECQL gene and providing a therapy to the subject when the presence of at least one mutation in the RECQL gene is detected, wherein the therapy comprises administering to the subject a therapeutic agent to treat the breast cancer and the therapeutic agent comprises a TOP1 inhibitor.

2. A method for treating breast cancer in a subject, comprising analyzing a diagnostic sample of the subject for the presence of at least one mutation in the RECQL gene and providing a therapy to the subject when the presence of at least one mutation in the RECQL gene is detected, wherein the therapy comprises administering to the subject a therapeutic agent to treat the breast cancer and the therapeutic agent down-regulates the expression of the RECQL gene having at least one mutation.

3. A method for treating breast cancer in a subject, comprising analyzing a diagnostic sample of the subject for the presence of at least one mutation in the RECQL gene and providing a therapy to the subject when the presence of at least one mutation in the RECQL gene is detected, wherein the therapy comprises administering to the subject a TOP1 inhibitor and a down-regulator of expression of the RECQL gene having at least one mutation.

4. The method of claim 1, wherein the at least one mutation comprises a missense variant, truncating mutation, nonsense mutation, essential splicing site mutation, frame shift insertion or deletion, or start codon change mutation.

5. The method of claim 1, wherein the at least one mutation causes a change in the amino acid sequence of the RECQL protein.

6. The method of claim 1, wherein the step of analyzing the sample comprises:
   isolating nucleic acid from the sample;
   amplifying the isolated nucleic acid using primers that are specific for or capable of amplifying a sequence corresponding to the RECQL gene; and
   sequencing the amplified nucleic acid.

7. The method of claim 1, wherein the change in the amino acid sequence causes a change in the secondary structure of the RECQL protein.

8. The method of claim 2, wherein the at least one mutation comprises a missense variant, truncating mutation, nonsense mutation, essential splicing site mutation, frame shift insertion or deletion, or start codon change mutation.

9. The method of claim 2, wherein the at least one mutation causes a change in the amino acid sequence of the RECQL protein.

10. The method of claim 2, wherein the step of analyzing the sample comprises:
    isolating nucleic acid from the sample;
    amplifying the isolated nucleic acid using primers that are specific for or capable of amplifying a sequence corresponding to the RECQL gene; and
    sequencing the amplified nucleic acid.

11. The method of claim 2, wherein the change in the amino acid sequence causes a change in the secondary structure of the RECQL protein.

12. The method of claim 3, wherein the at least one mutation comprises a missense variant, truncating mutation, nonsense mutation, essential splicing site mutation, frame shift insertion or deletion, or start codon change mutation.

13. The method of claim 3, wherein the at least one mutation causes a change in the amino acid sequence of the RECQL protein.

14. The method of claim 3, wherein the step of analyzing the sample comprises:
    isolating nucleic acid from the sample;
    amplifying the isolated nucleic acid using primers that are specific for or capable of amplifying a sequence corresponding to the RECQL gene; and
    sequencing the amplified nucleic acid.

15. The method of claim 3, wherein the change in the amino acid sequence causes a change in the secondary structure of the RECQL protein.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: insertion of 10 amino acids in a RECQL protein

<400> SEQUENCE: 1

Met Tyr Lys Leu Ile His Tyr Ser Phe Arg
1               5                   10

<210> SEQ ID NO 2
<211> LENGTH: 17
<212> TYPE: DNA
<213> ORGANISM: Artificial Sequence
```

```
<220> FEATURE:
<223> OTHER INFORMATION: internal probe specific to an allele

<400> SEQUENCE: 2
tcatccacag caattcg                                                   17

<210> SEQ ID NO 3
<211> LENGTH: 17
<212> TYPE: DNA
<213> ORGANISM: Artificial Sequence
<220> FEATURE:
<223> OTHER INFORMATION: internal probe specific to an allele

<400> SEQUENCE: 3
tcatccacag caattca                                                   17

<210> SEQ ID NO 4
<211> LENGTH: 24
<212> TYPE: DNA
<213> ORGANISM: Artificial Sequence
<220> FEATURE:
<223> OTHER INFORMATION: oligonucleotide used for amplification

<400> SEQUENCE: 4
gctcttcatt ggagtatctg tttg                                           24

<210> SEQ ID NO 5
<211> LENGTH: 20
<212> TYPE: DNA
<213> ORGANISM: Artificial Sequence
<220> FEATURE:
<223> OTHER INFORMATION: primer (1665F)

<400> SEQUENCE: 5
gacaacctga aagaataatg                                                20

<210> SEQ ID NO 6
<211> LENGTH: 20
<212> TYPE: DNA
<213> ORGANISM: Artificial Sequence
<220> FEATURE:
<223> OTHER INFORMATION: primer (1665r)

<400> SEQUENCE: 6
tggagaagat tattgcacac                                                20

<210> SEQ ID NO 7
<211> LENGTH: 21
<212> TYPE: DNA
<213> ORGANISM: Artificial Sequence
<220> FEATURE:
<223> OTHER INFORMATION: probe (1665del)

<400> SEQUENCE: 7
gtttgtacat aagatactgc t                                              21

<210> SEQ ID NO 8
<211> LENGTH: 23
<212> TYPE: DNA
<213> ORGANISM: Artificial Sequence
<220> FEATURE:
<223> OTHER INFORMATION: probe (1665wt)

<400> SEQUENCE: 8
gtttgtacat acttaagata ctg                                            23
```

```
<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
aagcaaatgt cgtcgtgtgt                                               20

<210> SEQ ID NO 10
<211> LENGTH: 20
<212> TYPE: DNA
<213> ORGANISM: Artificial Sequence
<220> FEATURE:
<223> OTHER INFORMATION: reverse primer

<400> SEQUENCE: 10
cagccctgaa agagttctgc                                               20
```